(12) United States Patent
Høgset et al.

(10) Patent No.: US 7,521,239 B2
(45) Date of Patent: Apr. 21, 2009

(54) PHOTOCHEMICAL INTERNALIZATION FOR VIRUS-MEDIATED MOLECULE DELIVERY INTO THE CYOSOL

(75) Inventors: Anders Høgset, Oslo (NO); Kristian Berg, Heggedal (NO); Gunhild Mari Mælandsmo, Oslo (NO); Birgit Øvstebø Engesæter, Oslo (NO); Lina Prasmickaite, Oslo (NO)

(73) Assignee: PCI Biotech AS (NO)

( * ) Notice: Subject to any disclaimer, the term of this patent is extended or adjusted under 35 U.S.C. 154(b) by 0 days.

(21) Appl. No.: 10/433,134

(22) PCT Filed: Nov. 29, 2001

(86) PCT No.: PCT/GB01/05281

§ 371 (c)(1),
(2), (4) Date: Nov. 28, 2003

(87) PCT Pub. No.: WO02/44395

PCT Pub. Date: Jun. 6, 2002

(65) Prior Publication Data

US 2004/0096425 A1  May 20, 2004

(30) Foreign Application Priority Data

Nov. 29, 2000 (GB) ................. 0029142.7
Dec. 1, 2000 (GB) ................. 0029405.8
Jun. 15, 2001 (GB) ................. 0114696.8

(51) Int. Cl.
*C12N 15/00* (2006.01)
*C12N 15/86* (2006.01)
*C12N 15/87* (2006.01)
*C12N 13/00* (2006.01)
*A01N 63/00* (2006.01)

(52) U.S. Cl. .............. 435/455; 435/173.5; 435/456; 435/460; 424/93.6; 514/44

(58) Field of Classification Search ........... None
See application file for complete search history.

(56) References Cited

U.S. PATENT DOCUMENTS

| 5,368,841 A * | 11/1994 | Trauner et al. .......... 514/183 |
| 5,521,291 A * | 5/1996 | Curiel et al. .......... 530/391.7 |
| 5,756,673 A * | 5/1998 | Sonenshein et al. ....... 530/350 |
| 5,876,989 A * | 3/1999 | Berg et al. ............ 435/173.7 |
| 6,224,870 B1 * | 5/2001 | Segal ................... 424/192.1 |
| 6,680,301 B2 * | 1/2004 | Berg et al. ............ 514/44 |

FOREIGN PATENT DOCUMENTS

| GB | 2 209 468 | 5/1989 |
| NO | 176786 | 5/1985 |
| NO | 173319 | 4/1986 |
| NO | 891491 | 4/1989 |
| NO | 176947 | 3/1990 |
| NO | 176645 | 6/1990 |
| NO | 900731 | 6/1990 |
| NO | 300499 | 10/1992 |
| NO | 301981 | 12/1993 |
| NO | 180742 | 4/1994 |
| WO | WO 95/07077 | 3/1995 |
| WO | WO 96/07432 | 3/1996 |
| WO | WO 96/28412 | 9/1996 |
| WO | WO 98/30242 | 7/1998 |
| WO | WO 00/53722 | 9/2000 |
| WO | WO 0054802 | 9/2000 |
| WO | WO 02/09690 | 2/2002 |

OTHER PUBLICATIONS

Verma et al (Nature 389: 239-242, 1997).*
Anderson (Nature 392:25-30), 1998).*
Romano et al (Stem Cells 18: 19-39, 2000).*
Somia and Verma (Nature Reviews Genetics 1: 91-99, 2000).*
Babincova et al (Med. Hypoth. 54(2): 180-181, 2000).*
Wang et al (J. Neuropath. Exp. Neuro. 58(8): 847-858, 1999).*
Lilge et al (J. Clin. Laser Med. Surgery 16(2): 81-91, 1998).*
Fasbender et al (J. Biol. Chem.272(10): 6479-6489, 1997).*
Clark et al (Cancer Gene Therapy 6(5): 437-446, 1999).*
Galipeau et al (Cancer Res 59: 2384-2394, May 15, 1999).*
Hodgson et al (Nature Biotech. 14: 339-342, 1996).*
Miller et al. (FASEB J. 9: 190-199, 1995).*
Deonarain (Exp. Opin. Ther. Patents 8(1):53-69, 1998).*
Knipe (in Fundamentals of Virology (Fields and Knipe Eds.), Raven Press, 1991).*
Crystal (Science 270: 404-410, 1995).*
Pouton et al (Adv. Drug Del. Rev. 46: 187-203, 2001).*
Read et al (Adv. Gen. 53:19-46, 2005).*
Wang et al (Neurochem. Int. 37(1): 1-6, Jul. 2000).*
Bonsted et al (Anticancer Res. 25:291-298, 2005).*
Akhlynina et al (Int. J. Cancer 81: 734-740, 1999).*
David T. Curiel; "High-Efficiency Gene Transfer Employing Adenovirus-Polylysine-DNA Complexes";Natural Immunity, Karger Medical and Scientific Publishers, Basel, CH, vol. 13 No. 2/3 1994; pp. 141-164.
Matt Cotten, et al.; "High efficiency receptor-mediated delivery of small and large (48 kilobase gene constructs using the endosome-disruption activity of defective or chemically inactivated adenovirus particles" Proc. Natl. Acad. Sci. USA; Jul. 1, 1992; 89(13):6094-8
Lina Rasmickaite, et al; Role of endosomes in gene transfection mediated by photochemical internalisation (PCI): The Journal of Gene Medicine 2000; Nov.-Dec.; 2(6):477-88.

(Continued)

Primary Examiner—Richard Schnizer
(74) Attorney, Agent, or Firm—Cantor Colburn LLP

(57) ABSTRACT

A method for introducing a molecule into the cytosol of a cell in which the cell is contacted with a photosensitizing agent, the cell is irradiated with light of a wavelength effective to activate the photosensitizing agent and, substantially at the same time or after the irradiation, the cell is contacted with the molecule to be introduced, particularly for use in cancer treatment, gene therapy and vaccination.

30 Claims, 11 Drawing Sheets

OTHER PUBLICATIONS

A. Baker, et al.; "Polyethylenimine (PEI) is a simple, inexpensive and effective reagent for condensing and linking plasmid DNA to adenovirus for gene delivery"; Gene Therapy 1997; Aug.; 4(8):773-82

Jiin H. Felgner, et al.; "Enhanced Gene Delivery and Mechanism Studies with a Novel Series of Cationic Lipid Formulations"; The Journal of Biological Chemistry; Jan. 28, 1994; 269(4): 2550-61.

Andrey A. Rosenkranz, et al; "Targeted intracellular delivery of photosensitizers to enhance photodynamic efficiency"; Immunology and Cell Biology (Aug. 2000); 78(4):n 452-64.

W. French Anderson; "Human gene therapy"; Nature 1998; 392: 25-30.

Kristian Berg, et al.; "Lysosomes and Microtubules as Targets for Photochemotherapy of Cancer"; Photochemistry and Photobiology 1997; 65: 403-409.

David T. Curiel; "Strategies to Adapt Adenoviral Vectors for Targeted Delivery"; Ann. NY Acad. Sci. 1999; 886: 158-171.

Thomas J. Dougherty, et al.; "Photodynamic Therapy"; Journal of the National Cancer Institute 1998, vol. 90, No. 12; Jun. 17; 90(12): 889-905.

Urs F. Greber, et al.; "Stepwise Dismantling of Adenovirus 2 during Entry into Cells"; Cell 1993, 75: 477-486.

Philip L. Leopold, et al.; "Fluorescent Virions: Dynamic Tracking of te Pathway of Adenoviral Gene Transfer Vectors in Living Cells"; Human Gene Therapy 1998; 9:367-378.

Inder M. Verma, et al.; "Gene Therapy-promises, problems and prospects"; Nature 1997, vol. 389: 239-242.

O Wildner, et al.; "Adenoviral vectors capable of replication improve the efficacy of HSVtk/GCV suicide gene therapy of cancer"; Gene Therapy 1999; 6: 57-62.

Chapter entitled "Gene therapy and other molecular genetic-based therapeutic approaches"; Chapter 20, pp. 551-587.

LG Baron, et al; "Cationic lipids are essential for gene delivery medicated by intravenous administration of lipoplexes"; Gene Therapy Jun. 1999; 6(6): 2179-83.

Karim Benihoud, et al.; "Adenovirus vectors for gene delivery"; Current Opinion in Biotechnology Oct. 1999; 10(5): 440-7.

Kristian Berg, et al; "Lysosomes as Photochemical Targets"; Int. J. Cancer 1994; 59: 814-822.

K. Berg, et al.; "Verapamil enhances the uptake and the photocytotoxic effect of PII, but not that of tetra (4-sulfonatophenyl) prophine"; Biochimica et Biophysica Acta 1998; 1370: 317-324.

Kristian Berg, et al.; "Photochemical Internalization: A Novel Technology for Delivery of Macromolecules into Cytosol"; Cancer Research 1999; 59: 1180-1183.

K. Berg, et al.; "Photochemical Internalisation: A novel technology for improsing macromolecule-based therapy"; Photodynamic News 2001; 4: 2-5.

Gianfranco Canti, et al.; "Antitumor immunity induced by photodynamic therapy with aluminum disulfonated phthalocyanines and laser light"; Anti-Cancer Drugs 1994; 5: 443-447.

P.J. Carter, et al.; "Adeno-associated viral vectors as gene delivery vehicles (Review)"; International Journal of Molecular Medicine Jul. 2000; 6(1): 17-27.

Luc Dekie, et al.; "Poly-L-glutamic acid derivatives as vectors for gene therapy"; Journal of Controlled Release Mar. 1, 2000; 65(1-2): 187-202.

Stefaan C. De Smedt, et al.; "Cationic Polymer Based Gene Delivery Systems"; Pharmaceutical Research Feb. 2000; 17(2): 113-26.

Wil J. A. de Vree, et al.; "Evidence for an Important Role of Neutrophils in the Efficacy of Photonamic Therapy in Vivo"; Cancer Research 1996; 56: 2908-2911.

Marco Folini, et al.; "Photochemical Internalization of a Peptide Nucleic Acid Targeting the Catalytic Subunit; of Human Telomerase"; Cancer Research 2003; 63: 3490-3494.

J. Gagnebin, et al.; "A photosensitising adenovirus for photodynamic therapy"; Gene Therapy 1999; 6: 1742-1750.

Martin C. Garnett; "Gene-Delivery Systems Using Cationic Polymers"; Critical Reviews in Therapeutic Drug Carrier Systems 1999; 16(2): 147-207.

Michael J. Grace, et al.; "The Use of Laser Scanning Cytometry of Assess Depth of Penetration of Adenovirus p53 Gene Therapy in Human Xenograft Biopsies"; American Journal of Pathology 1999, vol. 155, No. 6, 155: 1869-1878.

Jonathan Hansen, et al.; "Impaired Intracellular Trafficking of Adeno-Associated Virus Type 2 Vectors Limits Efficient Transduction of Murine Fibroblasts"; Journal of Virology 2000; 74: 992-996.

Anders Hogset, et al.; "Photochemical Transfection: A New Technology for Light-Induced, Site-Directed Gene Delivery"; Human Gene Therapy 2000; 11:869-880.

Shigeru Kawakami, et al.; "In Vivo Gene Delivery to the Liver Using Novel Galactosylated Cationic Liposomes"; Pharmaceutical Research 2000; vol. 17, No. 3; 17(3): 306-13.

Mladen Korbelik, et al.; "Photodynamic Therapy-mediated Immune Response against Subcutaneous Mouse Tumers"; Cancer Research 1999; 59: 1941-1946.

Miroslav Lapes, et al.; Photodynamic therapy of cutaneous metastases of breast cancer after local application of meso-tetra-(para-sulphophenyl)-porphin (TPPS); Journal of Photochemistry and Photobiology B 1996; 35: 205-207.

Mark S. Lesney; "Genetic Transportation"; Modern Drug Discovery; Oct. 2000; 55-60.

David H. Lynch, et al.; "Systemic Immunosuppression Induced by Photodynamic Therapy (PDT) is Adoptively Transferred by Macrophages"; Photochemistry and Photobiology 1989; vol. 49 No. 4; 49: 453-458.

Ram I. Mahato; "Pharmaceutical Perspectives of Nonviral Gene Therapy"; Advanced in Genetics, vol. 41: 95-156, 1999.

Johan Moan, et al.; "The Photodegradation of Porphyrins in Cells can be used to Estimate the Lifetime of Singlet Oxygen"; Photochemistry and Photobiology 1991; vol. 53, No. 4; 549-553.

Johan Moan, et al.; "Sulfonated Aluminium Phthalocyanines as Sensitizers for Photochemotherapy. Effects of Small Light Doses on Localization, Dye Fluorescence and Photosensitivity in V79 Cells"; Int. J. Cancert 1994; 58: 865-870.

Nadia Normand, et al.; "Particle Formation by a Conserved Domain of the Herpes Simplex Virus Protein VP22 Facilitating Protein and Nucleic Acid Delivery"; The Journal of Biological Chemistry 2001; 276: 15042-15050.

Maria Palasis, et al.; "Analysis of Adenoviral Transport Mechanisms in the Vessel Wall and Optimization of Gene Transfer Using Local Delivery Catheters"; Human Gene Therapy 2000; 11: 237-246.

Lina Prasmickaite, et al.; "Evaluation of Different Photosensitizers for Use in Photochemical Gene Transfection"; Photochemistry and Photobiology 2001; 73(4): 388-395.

Pal Kristian Selbo, et al.; "Release of gelonin from endosomes and lysosomes to cytosal by photochemical internalization"; Biochimica et Biophysica Acta 2000; 1475: 307-313.

Pal Kristian Selbo, et al.; Photochemical Internalisation Increases the Cytotoxic Effect of the Immunotoxin MOC31-Gelonin; Int. J. Cancer 2000; 87: 853-859.

Pal Kristian Selbo, et al.; "5-Aminolevulinic Acid-based Photochemical Internalization of the Immunotoxin MOC31-gelonin; Generates Synergistic Cytotoxic Effects in Vitro"; Photochemistry and Photobiology 2001; 74(2): 303-310.

Pal Kristian Selbo, et al., "In Vivo Documentation of Photochemical Internalization, A Novel Approach to Site Specific Cancer Therapy"; Int. J. Cancer 2001; 92: 761-766.

Manmohan Singh, et al.; "Cationic microparticles: A potent delivery system for DNA vaccines"; Proc. Natl. Acad. Sci. USA Jan. 18, 2000; 97(2): 811-6.

Nancy Smyth Templeton, et al.; "New Directions in Liposome Gene Delivery"; Molecular Biotechnology Apr. 1999; 11(2): 175-80.

Lutz Thilo, et al.; "Maturation of early endosomes and vesicular traffic to lysosomes in relation to membrane recycling"; Journal of Cell Science 1995; 108: 1791-1803.

TJ Wickham; "Targeting adenovirus"; Gene Therapy 2000; 7: 110-114.

Hogset et al.; "Light-Induced Adenovirus Gene Transfer, An Efficient and Specific Gene Delivery Technology for Cancer Gene Therapy"; Cancer Gene Therapy; 9: 365-371 (2002).

Bonsted, A. e al., "Photochemical Enhancement of Gene Delivery to Glioblastoma Cells is Dependent on the Vector Applied," Anticancer Research (2005) 25: 291-298.

* cited by examiner

PHOTOCHEMICAL INTERNALIZATION FOR VIRUS-MEDIATED MOLECULE DELIVERY INTO THE CYOSOL

CROSS-REFERENCE TO RELATED APPLICATIONS

This application is a National Stage entry filed under 35 USC 371 of International Application PCT/GB01/05281, filed Nov. 29, 2001, which claims foreign priority to United Kingdom Applications 0114696.8 filed Jun. 15, 2001, 0029405.8 filed Dec. 1, 2000, and 0029142.7 filed Nov. 29, 2000.

BACKGROUND

The present invention relates to a method of introducing molecules into cells using a photosensitising agent and irradiation of cells with light of a wavelength effective to activate the photosensitising agent, wherein the molecule to be introduced is associated with a viral carrier and in particular an adenovirus carrier. The present invention further relates to the use of this method in gene therapy.

Gene therapy, i.e. the genetic modification of the cells of a patient in order to combat disease, is recognized as having a large therapeutic potential for treating a variety of diseases, such as cancer, infectious diseases including viral and bacterial infections, cardiovascular disease, inherited disorders such as cystic fibrosis, immune system disorders and many other conditions. The clinical development of gene therapy is, however, still faced with many unsolved challenges, of which one of the most important is to find methods for efficient and specific delivery of therapeutic genes to the target cells in vivo (Verma & Somia, 1997, Nature, vol. 389, 239-242 and Anderson, 1998, Nature vol. 392, 25-30).

Gene therapy can involve many different possible approaches and can involve transfer of cloned human genes or gene segments, double stranded human genes or gene segments, genes from other genomes and organisms, oligonucleotides and various artificial genes or fragments thereof such as antisense genes.

In current methods many different carriers or vectors have been suggested for use in achieving gene transfer in gene therapy. As examples polycationic compounds, cationic lipids and viral systems can be mentioned, but as yet in vivo gene therapy has met with little success. Among the many known drawbacks of the current methods are low serum stability of the vector, limited specificity in gene delivery, low efficiency in gene delivery etc. The use of viral carriers has been approached with particular caution due to the introduction of viral elements into hosts which can cause adverse effects such as inflammation, which is not offset by enhanced transfer compared to other methods.

The majority of molecules do not readily penetrate cell membranes. Methods for introducing molecules into the cytosol of living cells are known in the art and are useful tools for manipulating and studying biological processes. Among the most commonly used methods are microinjection, red blood cell ghost-mediated fusion and liposome fusion, osmotic lysis of pinosomes, scrape loading, electroporation, calcium phosphate and virus-mediated transfection. These techniques are useful for manipulating cells in culture, although in many cases they may be impractical, time consuming, inefficient or they may induce significant cell death. Thus such techniques are not optimal for use in biological or medical research, or in therapies, where they are often not sufficiently efficient, may have intolerable toxic effects or may not be applicable for technical reasons.

It is well known that porphyrins and many other photosensitizing compounds may induce cytotoxic effects on cells and tissues. These effects are based upon the fact that upon exposure to light the photosensitizing compound may become toxic or may release toxic substances such as singlet oxygen or other oxidising species which are damaging to cellular material or biomolecules, including the membranes of cells and cell structures, and such cellular or membrane damage may eventually kill the cells. These effects have been utilised in the treatment of various abnormalities or disorders, including especially neoplastic diseases. The treatment is named photodynamic therapy (PDT) and involves the administration of photosensitizing (photochemotherapeutic) agents to the affected area of the body, followed by exposure to photoactivating light in order to activate the photosensitizing agents and convert them into cytotoxic form, whereby the affected cells are killed or their proliferative potential diminished. Photosensitizing agents are known which will localise preferentially or selectively to the desired target site e.g. to a tumour or other lesion.

A range of photosensitizing agents are known, including notably the psoralens, the porphyrins, the chlorins and the phthalocyanins. Such drugs become toxic when exposed to light.

Porphyrin photosensitisers act indirectly by generation of toxic oxygen species, and are regarded as particularly favourable candidates for PDT. Porphyrins are naturally occurring precursors in the synthesis of heme. In particular, heme is produced when iron ($Fe^{3+}$) is incorporated in protoporphyrin IX (PpIX) by the action of the enzyme ferrochelatase. PpIX is an extremely potent photosensitizer, whereas heme has no photosensitizing effect. A variety of porphyrin-based or porphyrin-related photosensitisers are known in the art and described in the literature.

The cytotoxic effect is mediated mainly through the formation of singlet oxygen. This reactive intermediate has a very short lifetime in cells (<0.04 µs). Thus, the primary cytotoxic effect of PDT is executed during light exposure and very close to the sites of formation of $^1O_2$. $^1O_2$ reacts with and oxidizes proteins (histidine, tryptophan, methionine, cysteine, tyrosine), DNA (guanine), unsaturated fatty acids and cholesterol. One of the advantages of PDT is that tissues unexposed to light may be left unaffected ie. that a selective PDT effect may be obtained. There is extensive documentation regarding use of PDT to destroy unwanted cell populations, for example neoplastic cells. The patent literature describes a number of photodynamic compounds, alone or conjugated with targeting agents, e.g. immunoglobulins directed to neoplastic cell receptor determinants, making the complex more cell specific. Certain photochemical compounds, such as hematoporphyrin derivatives, have furthermore an inherent ability to localise in malignant cells. Such methods and compounds, are described in the Norwegian patent No. 173319 and in Norwegian patent applications Nos. 90 0731, 176 645, 176 947, 180 742, 176 786, 301 981, 30 0499 and 89 1491. Such PDT methods are thus dependent on the destruction of cell structures leading to cell death.

WO 96/07432 or the copending application WO 00/54802 on the other hand, are concerned with methods which use the photodynamic effect as a mechanism for introducing otherwise membrane-impermeable molecules into the cytosol of a cell in a manner which does not necessarily result in widespread cell destruction or cell death. In these methods, the molecule to be internalised and a photosensitising compound are applied simultaneously or in sequence to the cells, upon which the photosensitizing compound and the molecule are endocytosed or in other ways translocated into endosomes, lysosomes or other intracellular membrane restricted compartments.

The molecule to be translocated and the photosensitising compound are applied to the cells together or sequentially (preferably separately and sequentially) and are taken up by the cell together into the same intracellular compartments (i.e. are co-translocated). The molecule to be internalised within the cell is then released by exposure of the cells to light of suitable wavelengths to activate the photosensitising compound which in turn leads to the disruption of the intracellular compartment membranes and the subsequent release of the molecule, which is located in the same compartment as the photosensitizing agent, into the cytosol. This method was termed "photochemical internalisation" or PCI. Thus, in these methods the final step of exposing the cells to light results in the molecule in question being released from the same intracellular compartment as the photosensitizing agent and becoming present in the cytosol.

It was believed that in order for this technique to be effective it was essential that both the photosensitising compound and the molecule to be released into the cytosol were present in the same intracellular compartments when irradiation was performed. However, it has since been found that molecules can be introduced into the cytosol of cells by similar PCI methods but where the exposure of the cells to light is not necessarily the final step and the methods are not dependent on the transfer molecule and the photosensitizing agent being located in the same intracellular compartments at the time of light exposure. In such methods the photosensitising agent may be contacted with the cells and activated by irradiation before the molecule to be internalised and thus delivered to the cytosol is brought into contact with the cells. Thus, despite the fact that the molecule to be internalised and the photosensitising agent are not necessarily localised in the same intracellular compartments at the time of light exposure, the molecule still enters the cell and is delivered to the cytosol. These results are described in detail in the co-pending international application (filed on 29 Nov. 2001 in the name of The Norwegian Radium Hospital Research Foundation, entitled "Method"), a copy of which is appended hereto and is incorporated herein by reference.

Surprisingly it has now been found that the use of PCI techniques in combination with viral vectors can substantially improve the virus mediated gene delivery to a cell. Since photochemical treatments are in clinical use (Dougherty et al, 1998, J. Natl. Cancer Inst, vol. 90, 889-905), and generally are very specific and have few side effects, the technology described has a clear potential for improving both the efficiency and the specificity of in vivo gene therapy.

BRIEF SUMMARY OF THE INVENTION

Thus, the present invention provides a method for introducing a molecule into a cell, said method comprising contacting said cell with a photosensitising agent, contacting said cell with the molecule to be introduced which is associated with a viral carrier, and irradiating said cell with light of a wavelength effective to activate the photosensitising agent.

These steps can be carried out in any appropriate order providing that the eventual result is the cellular uptake of the viral carrier and hence the molecule to be introduced into the cell and internalization of that molecule. No other molecules except the viral carrier and the photosensitizing agent are required for performance of the invention.

DETAILED DESCRIPTION OF THE INVENTION

The term "cell" is used herein to include all eukaryotic cells including insect cells and fungal cells and including somatic and germ cells. Representative "cells" thus include all types of mammalian and non-mammalian animal cells, plant cells, insect cells, fungal cells, protozoa and protoplasts and preferably mammalian cells such as human, mouse, rat, cat, dog, sheep, horse, cow or goat cells.

"Internalisation" as used herein, refers to the delivery of the molecules to be introduced into the cells (sometimes referred to herein as the "transfer molecules"), with or without the viral carrier still attached, to the cytosol. In the present case "internalisation" thus includes the step of release of the molecule to be introduced, optionally in association with all or part of its viral carrier, from intracellular/membrane bound compartments into the cytosol and may thereafter be transferred to the nucleus. Once internalized the molecule is considered to have been "introduced" into the cell in accordance with the method of the invention.

The intracellular membrane-restricted compartment may be any such compartment which is present in a cell.

Preferably the compartment will be a membrane vesicle, especially an endosome or a lysosome. However, the intracellular compartment may also include the Golgi apparatus or the endoplasmic reticulum.

As used herein, "cellular uptake" or "translocation" refers to one of the steps of internalisation in which molecules or entities external to the cell membrane are taken into the cell such that they are found interior to the outer-lying cell membrane, e.g. by endocytosis or other appropriate uptake mechanisms, for example into or associated with an intracellular membrane-restricted compartment, for example the endoplasmic reticulum, Golgi body, lysosomes, endosomes etc.

Appropriate "molecules" to be introduced into the cell can be any that can be associated with viral carriers, viral vectors or virus particles and are sometimes referred to herein as "transfer molecules". Such molecules are generally nucleic acid molecules and may comprise a full length gene to be introduced into the cell or a functional fragment thereof or may be for example a cDNA sequence containing the complete coding sequence of a gene or a functional fragment thereof. Alternatively, said nucleic acid molecules may encode antisense RNA molecules, ribozymes, aptamers, oligonucleotides or triplex forming oligonucleotides, or comprise transcription factor "decoy" DNA and so on. Preferably the nucleic acid molecules are from 10 to 30 000 bases in length, e.g. 20-10000 bases in length.

"Associated with" as used herein refers to a molecule which is incorporated into or connected in some way to a viral carrier, viral vector or viral particle e.g. incorporated within the genome of said viral molecule or separate to said genome but carried within the viral particle. Generally the molecules to be introduced into the cells will be packaged or incorporated within viral particles, i.e. encapsulated or incorporated within a viral coat or capsid. Preferably the molecule to be transported is a polynucleotide and is preferably inserted within a viral construct which contains certain viral derived elements necessary to enable the construct to become packaged inside the viral carrier. The molecule to be transported may for example be cloned into a cloning site on the viral carriers' genome. Alternatively 2 or more separate molecules contributing these features may be used as described hereinbelow. Such viral particles may be selected such that they may or may not be able to infect the cells of their own accord and, if they can infect the cells of their own accord, once they have been internalized within the cell they may be selected such that they may or may not be able to harness the endogenous cellular machinery in order to replicate and assemble new virus packages to be secreted from the cell. However, generally, when used for gene therapy or other in vivo applications, for safety reasons viral vectors are usually disabled so that they can infect host cells but cannot replicate, assemble new virions and infect new cells, i.e. made replication incompetent.

Such disablement can be carried out by any appropriate means, but is conveniently done by deleting some of the viral genes required for viral replication and optionally inserting the therapeutic genes which are to be transferred in their place. However, the technology described in this application can also be used with replication-competent or replication-restricted viruses, such as e.g. the ONYX-15 (Khuri F. R. et al., (2000), Nature Med. 6, 879-885) or herpes simplex virus thymidine kinase encoding replication-restricted adenoviruses such as described by Wildner and coworkers (Wildner O. et al., (1999) Gene Ther. 6, 57-62; Wildner O. et al., (1999), Cancer Res. 59, 410-413), or e.g. replicating retroviruses as described by D. Klatzman (oral presentation and abstract at the 8th Meeting of the European Society of Gene Therapy, Stockholm 7-10 Oct. 2000).

The whole molecular entity to be introduced into the cell, i.e. the viral carrier incorporating or encapsulating the molecule to be introduced is sometimes referred to herein as the "transfer particle".

Generally the nucleic acid which is to be introduced into the cell by the methods of the present invention is part of a viral based construct, e.g. a viral based plasmid which contains certain viral derived elements necessary to enable the construct to become packaged inside the viral carrier/viral capsid/viral vector. Alternatively however, the nucleic acid to be introduced may form part of one molecule, e.g. a plasmid and a second molecule may be present which contains the sequences necessary for the development of the viral carrier which contains the first molecule. In addition, if the action of the nucleic acid within the cell is dependent on the expression of the protein encoded thereby or the production of RNA therefrom, the nucleic acid is conveniently flanked by appropriate regulatory sequences (e.g. promoters) for ensuring high level expression in the particular target cell. Such regulatory elements may be derived from viruses (e.g. the CMV promoter from cytomegalovirus) or any other appropriate organisms and the design of appropriate viral constructs to enable good expression of the protein encoded by the nucleic acid molecule are well known to persons skilled in the art. For example, tissue specific or regulatable promoters can be used to obtain tissue or disease specific or regulatable expression. For example the tissue specific promoter melanoma specific tyrosinase promoter may be used. Regulatable promoters such as tetracylin-regulated promoters are well known. More examples of specific or regulated promoters that can be employed in the present invention can be found in Hart, I. R. (Semin. Oncol., 1996, 23, 154-158), Miller and Whelan (Hum. Gene Therapy, 1997), Nettelbeck and Muller (Trends Genet., 2000, 16, 174-181) and Spear (Anticancer Res., 1998, 18, 3223-3231) and the references therein.

The "viral carrier" molecule with which the transfer molecule is associated can be any viral system providing that the viral carriers of this system are capable of associating with, incorporating or encapsulating the molecules which are to be introduced into the cells. Thus, generally the transfer molecules are packaged within a viral particle or virus capsid and the terms "viral particle", "virus capsid" and "viral vector" are also used herein to mean "viral carrier" These terms as used herein do not include viral based plasmids or DNA, although such a plasmid may be used to create the viral carrier.

Examples of appropriate viral systems for use in the present invention are adenoviruses and adeno-associated viruses, retroviruses, lentiviruses, Herpes viruses, bacteriophages, influenza virus, Sendai virus, Vaccinia virus and Baculovirus, preferably adenoviruses, adeno-associated viruses, retroviruses, lentiviruses, and bacteriophages. Adenovirus is a preferred virus system for use in the methods of the present invention.

For use according to the invention viral carriers generally form modified forms of the naturally occurring viruses to add desired properties and minimise possible pathogenicity or other undesired side-effects. Thus, viral carriers represent variants of viruses routinely used for gene therapy and are well known in the art, but retain essential and identifiable components from the source virus.

As used herein "photosensitizing agent" refers to an agent which is photosensitive and which, on the application of photoactivating light, is converted to a cytotoxic form or gives rise to a cytotoxic species. The photosensitizing agent to be used according to the present invention (which is distinct and preferably different to the transfer molecule) is conveniently any such agent which localises to intracellular compartments, particularly endosomes or lysosomes. A range of such photosensitising agents are known in the art and are described in the literature, including in WO96/07432. Mention may be made in this respect of di- and tetrasulfonated aluminium phthalocyanine (e.g. $AlPcS_{2a}$), sulfonated tetraphenylporphines ($TPPS_n$), nile blue, chlorine $e^6$ derivatives, uroporphyrin I, phylloerythrin, hematoporphyrin and methylene blue which have been shown to locate in endosomes and lysosomes of cells in culture. This location is in most cases due to endocytic activity. Thus, the photosensitizing agent is preferably an agent which is taken up into the internal compartments of lysosomes or endosomes. However, other photosensitizing agents which locate to other intracellular compartments for example the endoplasmic reticulum or the Golgi apparatus may also be used. It is also conceivable that mechanisms may be at work where the effects of the photochemical treatment are on other components of the cell (i.e. components other than membrane-restricted compartments). Thus, for example one possibility may be that the photochemical treatment destroys molecules important for intracellular transport or vesicle fusion. Such molecules may not necessarily be located in membrane-restricted compartments.

Classes of suitable photosensitising agents which may be mentioned thus include porphyrins, psoralens, phthalocyanines, purpurins, chlorins, benzoporphyrins naphthalocyanines, cationic dyes, tetracyclines and lysomotropic weak bases or derivatives or precursors thereof (Berg et al., J. Photochemistry and Photobiology, 1997, 65, 403-409). Other suitable photosensitizing agents include texaphyrins, pheophorbides, porphycenes, bacteriochlorins, ketochlorins, hematoporphyrin derivative, and derivatives thereof, endogenous photosensitizers induced by 5-aminolevulinic acid and derivatives thereof, diners or other conjugates between photosensitizers.

Preferably the photosensitizer is in free form, ie. not conjugated to any other macromolecule. Especially preferably the photosensitizing agent is separate from the viral carrier, ie. is a discrete entity. However the photosensitizer may alternatively be associated with, attached to, or conjugated to, a carrier or other molecule as described hereinafter, e.g.

attached to a targeting antibody or coupled to a carrier such as polylysine. Alternatively, in certain circumstances, the photosensitizing agent may be attached to, associated with or conjugated to, the viral carrier or a part thereof (e.g. the surrounding lipid membrane e.g. of a retrovirus), directly.

Preferred photosensitising agents include $TPPS_4$, $TPPS_{2a}$, $AlPcS_{2z}$ and other amphiphilic photosensitizers.

In a preferred aspect, the present invention provides methods in which the photosensitizing agents are compounds being 5-aminolevulinic acid or esters of 5-aminolevulinic acids or pharmaceutically acceptable salts thereof.

In such esters the 5-amino group may be substituted or unsubstituted, the latter case being the ALA esters.

More particularly, the ALA esters for use according to the invention are esters of 5-aminolevulinic acids with optionally substituted alkanols, ie. alkyl esters or substituted alkyl esters.

Conveniently, ALA esters which may be used are compounds of formula I,

$$R_2^2N-CH_2COCH_2-CH_2CO-OR^1 \quad (I)$$

(wherein $R^1$ may represent alkyl optionally substituted by hydroxy, alkoxy, acyloxy, alkoxycarbonyloxy, amino, aryl, oxo or fluoro groups and optionally interrupted by oxygen, nitrogen, sulphur or phosphorus atoms; and $R^2$, each of which may be the same or different, represents a hydrogen atom or a group $R^1$) and salts thereof.

The substituted alkyl $R^1$ groups may be mono or poly-substituted. Thus suitable $R^1$ groups include for example unsubstituted alkyl, alkoxyalkyl, hydroxyalkoxyalkyl, polyhydroxyalkyl, hydroxy poly alkyleneoxyalkyl and the like. The term "acyl" as used herein includes both carboxylate and carbonate groups, thus, acyloxy substituted alkyl groups include for example alkylcarbonyloxy alkyl. In such groups any alkylene moieties preferably have carbon atom contents defined for alkyl groups below. Preferred aryl groups include phenyl and monocyclic 5-7 membered heteroaromatics, especially phenyl and such groups may themselves optionally be substituted.

Representative substituted alkyl groups $R^1$ include alkoxymethyl, alkoxyethyl and alkoxypropyl groups or acyloxymethyl, acyloxyethyl and acyloxypropyl groups eg. pivaloyloxymethyl.

Preferred ALA esters for use as photosensitizing agents according to the invention, include those wherein $R^1$ represents an unsubstituted alkyl group and/or each $R^2$ represents a hydrogen atom.

As used herein, the term "alkyl" includes any long or short chain, straight-chained or branched aliphatic saturated or unsaturated hydrocarbon group. The unsaturated alkyl groups may be mono- or polyunsaturated and include both alkenyl and alkynyl groups. Such groups may contain up to 40 carbon atoms. However, alkyl groups containing up to 10 eg. 8, more preferably up to 6, and especially preferably up to 4 carbon atoms are preferred.

Particular mention may be made of ALA-methylester, ALA-ethylester, ALA-propylester, ALA-hexylester, ALA-heptylester and ALA-octylester and salts thereof, which represent preferred photosensitizing agents for use according to the invention.

The methods of the present invention may be used in vitro or in vivo, either by systemic or local treatment in situ, or by ex vivo treatment followed by the administration of the treated cells to the body.

For performance of the method of the invention, the steps of "contacting" the cells with a photosensitising agent and separately with the viral carrier may be carried out in any convenient or desired way. Thus, if the contacting step is to be carried out in vitro the cells may conveniently be maintained in an aqueous medium such as for example appropriate cell culture medium and at the appropriate time point the photosensitising agent or viral carrier can simply be added to the medium under appropriate conditions, for example at an appropriate concentration and for an appropriate length of time.

The photosensitizing agent is brought into contact with the cells at an appropriate concentration and for an appropriate length of time which can easily be determined by a skilled person using routine techniques and will depend on the particular photosensitizing agent used and the cell type. The concentration of the photosensitizing agent must be such that once taken up into the cell (e.g. into, or associated with, one or more of its intracellular compartments) and activated by irradiation, one or more cell structures are disrupted e.g. one or more intracellular compartments are lysed or disrupted. For example photosensitising agents used in the Examples herein may be used at a concentration of for example 10 to 50 μg/ml. Generally for in vitro use the range can be much broader, e.g. 0.05-500 μg/ml. For in vivo human treatments the photosensitizing agent may be used in the range 0.05-20 mg/kg body weight when administered systemically or 0.1-20% in a solvent for topical application. In smaller animals the concentration range may be different and can be adjusted accordingly.

The time of incubation of the cells with the photosensitizing agent (i.e. the "contact" time) can vary from a few minutes to several hours, e.g. even up to 48 hours or longer. The time of incubation should be such that the photosensitizing agent is taken up by the appropriate cells.

The incubation of the cells with the photosensitizing agent may optionally be followed by a period of incubation with photosensitizing free medium before the cells are exposed to light or the transfer molecule is added.

The transfer molecule can be any nucleic acid molecule as discussed above and is brought into contact with the cells in association with a viral carrier at an appropriate concentration/dosage and for an appropriate length of time. An appropriate concentration of viral carrier can be determined depending on the efficiency of uptake of the carrier in question into the cells in question and the final concentration it is desired to achieve in the cells. One of the surprising advantages of the use of PCI in conjunction with a viral carrier is that lower doses of virus particles can be used to obtain the same efficiency of transfection e.g. up to 20 times fewer virus particles. Appropriate doses of virus carriers to be used will of course be dependent on the type of virus used, and, for in vivo applications, the mode of administration, the type of disease to be treated, whether or not targeting ligands are used (see below), etc. Typically for intratumoral injection of a non-replicative adenoviral vector $10^3$ to $10^{13}$ plaque forming units (pfus, infectious particles) would be injected per injection. This would usually correspond to about $10^5$ to $10^{15}$ virus physical particles, since in a "usual" virus preparation only about 1% of the virus physical particles give rise to infection. For replication-competent viruses doses even lower than those given above may be effective, e.g. as low as $10^3$ particles, e.g. $10^3$ to $10^6$, $10^{10}$ or $10^{15}$ particles may be used. On the other hand, where systemic administration is used it may be necessary to increase the dose.

A further advantage which has been observed is that greatly improved efficacy of transfection can be achieved, even up to 100% of all cells in the experiment being transfected. Using known methods, such levels were not previously possible or required prohibitively high virus doses. Thus, preferably, the methods of the invention achieve transfection of more than 50%, especially preferably more than 75, 85 or 95%, of the total cells.

Thus "transfection time" or "cellular uptake time" for the viral carriers, ie. the contact time of the carriers with the cell, can be a few minutes or up to a few hours, for example a transfection time of from 10 minutes until up to 10 or 24 hours, for example 15 minutes until up to 10 hours or for example 15 or 30 minutes until up to 2, 3, 4 or 6 hours can be used. An increased transfection time can result in increased uptake of the carrier in question.

Viral carriers may be applied before, after or simultaneously with irradiation. When applied after irradiation, viral carriers may be applied, for example, 0 to 4 or 0 to 24 hours after irradiation, e.g. more than 1, 2, 4, 8, 10 or even 12 hours after irradiation.

Optionally, after contact with the viral carrier, the cell may be transferred to carrier-free medium, e.g. before irradiation, e.g. for more than 5 minutes, such as for 15 minutes to 2 hours, e.g. for 30 minutes. When applied before irradiation, this may be, for example, in the 12 hours preceding irradiation, e.g. 15 minutes to 2 hours preceding irradiation, optionally with an interval in medium free of the viral carrier.

It will be appreciated that the time allowed for transfection through contact of the viral carrier with the cell is difficult to control in in vivo applications. However, contact time may be controlled by appropriate contact and washing step when performed ex vivo, in vitro or for some types of local administration.

The photosensitising agent and the viral carrier associated with the molecule to be introduced can be added separately or together to the cells in advance of light treatment/irradiation as described in WO96/07432, WO00/54802, and the copending application attached hereto (international patent application filed on 29 Nov. 2001 in the name of The Norwegian Radium Hospital Research Foundation, entitled "Method"), or the photosensitising agent can be added to the cells first, followed by the irradiation step and then the addition of the viral carrier as described in the copending application appended hereto. In the latter method preferably irradiation is performed prior to cellular uptake of the transfer molecule (here the viral carrier), especially preferably the transfer molecule is contacted with the cell after irradiation, e.g. 0 to 4 hours after irradiation. Alternatively, the cell is contacted with the transfer molecule at substantially the same time as irradiation.

In other words the irradiation step can either be performed prior to the cellular uptake of the viral carriers into any intracellular compartment or after such cellular uptake, providing that the photosensitising agent has been taken up into the intracellular compartments in advance of irradiation. If both the photosensitising agent and the viral carrier have been taken up into the intracellular compartments of the cell at the time of light exposure, then the viral carrier and the photosensitising agent may be located in the same or different intracellular compartments at the time of light exposure. Further detail on the timing of addition of the various components to the cells is discussed in the prior art documents WO96/07432 and WO00/54802 above or the copending application attached hereto, the contents of which are incorporated herein by reference.

In any event, the time window in which the viral carriers may be brought into contact with the cells and still be taken up and internalised by the cells may depend on a variety of factors such as for example the cell type, the particular carrier in question, the particular photosensitising agent used, and the duration of the light treatment. This time window can if necessary be determined for a particular set of conditions and would be well within the bounds of a person skilled in the art.

The time at which the viral carrier is administered will vary depending on whether the methods are being carried out in vitro or in vivo. For in vitro methods the viral carriers can generally be brought into contact with all the target cells simultaneously i.e. the time of administration coincides with the time of contact, e.g. if the cells are growing in an in vitro culture, and thus it is relatively easy to bring the carriers in contact with the cells at an appropriate time point. In vivo however, the step of contacting the target cells with the viral carriers is clearly more complicated and will depend on the mode of administration, the type of viral carrier and the location of the target cells. For example, where the viral carriers can be administered directly to the target cells, e.g. by injection, then the viral carriers will come into contact with the target cells (or at least a proportion of them) relatively quickly, e.g. in a matter of minutes or hours after administration.

If on the other hand the viral carriers are administered by intravenous injection for a distant target then these carriers may take a lot longer to come into contact with the target cells. For example they may take 24 to 96 hours after administration to reach the target cells. This "journey time" will have to be taken into account in deciding the appropriate time at which to administer the viral carriers relative to the administration of the photosensitizing agent and the time of irradiation. The same considerations of course apply to the time at which the photosensitising agent is administered. However, unlike for the transfer molecule, it is important that this agent should be administered sufficiently prior to irradiation such that on irradiation said agent has been taken up into an intracellular compartment. Thus conveniently said agent is applied 1 to 72 hours prior to irradiation, e.g. 4 to 72, such as 4 to 48 or 4 to 24 hours prior to irradiation. Again, as discussed above in connection with the step of bringing the viral carriers (and hence the transfer molecules) into contact with the cells, the timing of administration of the photosensitizing agent in relation to the time point of irradiation will depend on the time it will take for a photosensitizing agent to reach the target cells and be taken up by them. This time may vary depending on whether the methods are being carried out in vitro or in vivo and on whether the administration is direct to the target tissue or is at a distal site. In all cases, it is important that the photosensitizing agent has been taken up by the target cells before irradiation takes place. Said agent may be maintained in contact with said cells immediately up to irradiation, e.g. for 1 or 4 to 72 hours, preferably 4 to 24 hours, e.g. 12 to 20 hours, or may be removed from contact immediately prior to irradiation, e.g. for more than 5 minutes, e.g. for 10 minutes to 8 hours, e.g. 1 hour to 4 or 6 hours in agent-free medium and/or medium containing the transfer molecule.

Thus, although the situation in vivo is more complicated than in vitro, the underlying. concept of the present invention is still the same, i.e. that the administration times must be such that before irradiation occurs an appropriate amount of the photosensitizing agent has contacted and been taken up by the target cells and either: (i) before or during irradiation the transfer molecule (and its viral carrier) has either been taken up by the cells, or will be taken up after sufficient contact with the target cells, into the same or different intracellular compartments as the photosensitising agent or (ii) after irradiation the transfer molecule and its associated viral carrier is in contact with the cells for a period of time sufficient to allow its uptake into the cells.

Optionally, the photosensitising agent may be attached to, associated with or conjugated to one or more carrier molecules, targeting molecules or targeting vectors which can act to facilitate or increase the uptake of the photosensitising agent or can act to target or deliver these entities to a particular cell type, tissue or intracellular compartment. Examples of carrier systems include polylysine (e.g. poly-L-lysine or poly-D-lysine), polyethyleneimine or dendrimers (e.g. cationic dendrimers such as SuperFect®) or other polycations, dextran sulphate, different cationic lipids such as DOTAP or lipofection or cationic lipids formulated with a "helper lipid" such as DOPE, liposomes, reconstituted LDL-particles, sterically stabilised liposomes or different particles derived from viral systems such as for example adenovirus, lentiviruses and other retroviruses, adeno associated virus, bacteriophages etc. These carrier systems can generally improve the pharmacokinetics and increase the cellular uptake of the photosensitizing agent and may also direct the photosensitizing agent to intracellular compartments that are especially beneficial for obtaining photochemical internalisation, but they do not generally have the ability to target the photosensitizing agent to specific cells (e.g. cancer cells) or tissues.

The viral carriers may also be attached to, associated with or conjugated to one or more such carrier molecules, targeting molecules or targeting vectors. Alternatively some surface modifications of the viral carrier particle can be advantageous for use in the present invention. The potential benefits arising from the use of such carriers and/or surface modifications are: (i) improvement in the pharmacokinetics and biodistribution of the viral vector, usually by increasing the circulation time; (ii) camouflaging the virus's ability to bind to its normal receptor to make it possible to redirect the virus to other receptors (and thereby to tissues that are not normally infected by the virus); (iii) providing a positive surface charge on the viral vector so that it will bind to and infect a wider range of cells than by its natural infection mechanism; (iv) "hiding" the virus from the immune system.

Preferably the viral carrier is attached to, associated with or conjugated to a carrier molecule, preferably a carrier comprising polycations (e.g. polylysine or SuperFect®) or cationic lipids.

Examples of carriers which can be used in this regard are polycations (Lanuti M. et al. (1999), Gene The. 6 1600-1610; ArcasoyS. M. et al. (1997) Gene Ther. 4, 32-8; Dodds E. et al. (1999), J. Neurochem. 72, 2105-2122) and cationic lipids (Clark P. R. et al. (1999) Cancer Gene Ther. 6, 437-446). Examples of surface modifications which can be used in this regard are: polyethylene glycol (Croyle M. A. et al. (2000) Hum. Gene Ther. 11, 1713-1722) and poly-[N-(2-hydroxypropyl)-methacrylamide] based polymers (Seymour, L. et al. J. Gene Med. Suppl. to Vol 2(5), p. 52).

To achieve specific or selective targeting of the viral carrier molecules (and hence the transfer molecule) and/or the photosensitizer to particular cell types or tissues, these entities may be associated with or conjugated to specific targeting molecules that will promote the specific cellular uptake of the transfer molecule into desired cells or tissues. Such targeting molecules may also direct the transfer molecule and/or the photosensitizer to intracellular compartments that are especially beneficial for obtaining photochemical internalisation.

Many different targeting molecules can be employed, e.g. as described in Curiel, D. T. (1999), Ann. New York Acad. Sci. 886, 158-171; Bilbao, G. et al. (1998), in Gene Therapy of Cancer (Walden et al., eds., Plenum Press, New York), Peng K. W. and Russell S. J. (1999), Curr. Opin. Biotechnol. 10, 454-457, Wickham T. J. (2000), Gene Ther. 7, 110-114.

In addition, it is important to note that rather than having to attach them to specific carriers, it is known in the art that some photosensitising agents which are suitable for use in the methods of the present invention show an inherent preferential localisation to certain tissue sites. For example certain photosensitizing agents, such as hematoporphyrin derivatives, are known which localise preferentially or selectively to tumour tissues or other lesions. Several other examples are described in Boyle and Dolphin (Photochem. Photobiol. 64: 469-485 (1996)). Such preferential localisation can be harnessed in the methods of the present invention.

The targeting molecule may be associated, bound or conjugated to the viral carrier, to the photosensitizing agent or both, and the same or different carrier or targeting molecules may be used.

Such targeting molecules or carriers as described above may also be used to direct the viral carrier or the photosensitising agent to particular intracellular compartments especially beneficial for the employment of PCI, for example lysosomes or endosomes.

The transfer molecule is thought to initially remain in association with the viral carrier in the cytosol of the cells once the irradiation step has occurred which releases the transfer particles from the intracellular compartments. Once the transfer particles have been internalised into the cytosol of the cells, the events which occur will depend on the viral carrier system chosen. For example, in the case of adenovirus, usually the adenovirus particles (associated with the transfer molecule) migrate to the nucleus, after which the viral DNA (and hence the nucleic acid transfer molecule) enters the nucleus of the cell. In any event, where the nucleic acid transfer molecule is incorporated into a virus particle or carrier, after photochemical internalisation and possibly subsequent events depending on the viral carrier, the nucleic acid molecule should be present at the correct intracellular location so that the appropriate intracellular processing can occur to allow the introduced transfer molecule to perform its desired function. For example, if the transfer molecule encodes a desired protein then processing steps leading to the expression of this protein are required. If the transfer molecule is a DNA molecule which encodes an antisense RNA molecule then processing steps leading to the transcription of the RNA from the DNA are required, etc.

The light irradiation step to activate the photosensitising agent may take place according to techniques and procedures well known in the art. For example, the wavelength and intensity of the light may be selected according to the photosensitising agent used, preferably at a dose level of 40 to 200 J/cm$^2$, e.g. 100 J/cm$^2$ and at a wavelength of 300-800 nm, e.g. 500-700 nm. Suitable light sources are well known in the art. The time for which the cells are exposed to light and the doses of light used in the methods of the present invention may vary. In general, appropriate irradiation times and doses can be selected by a person skilled in the art to enable disruption of the intracellular compartments containing the photosensitiser and the subsequent uptake and/or release of transfer particles into the cytosol. The efficiency of the internalisation of the transfer particle into the cytosol appears to increase with increased exposure to light. A preferred length of time for the irradiation step depends on the photosensitizer, the amount of the photosensitizer accumulated in the target cells or tissue and the overlap between the absorption spectrum of the photosensitizer and the emission spectrum of the light source. Generally, the length of time for the irradiation step is in the order of minutes to several hours, e.g. preferably up to 60 minutes e.g. from 0.5 or 1 to 30 minutes, for example up to 10 or 15 minutes, e.g. from 0.5 to 3 minutes or from 3 to 10 minutes and preferably approximately 7 minutes, e.g. 6 to 8 minutes. Appropriate light doses can be selected by a person skilled in the art and again will depend on the photosensitizer and the amount of photosensitizer accumulated in the target cells or tissues. For example, the light doses typically used for photodynamic treatment of cancers with the photosensitizer Photofrin and the protoporphyrin precursor 5-aminolevulinic acid is in the range 50-150 J/cm$^2$ at a fluence range of less than 200 mW/cm$^2$ in order to avoid hyperthermia. The light doses are usually lower when photosensitizers with higher extinction coefficients in the red area of the visible spectrum are used. However, for treatment of non-cancerous tissues with less photosensitizer accumulated the total amount of light needed may be substantially higher than for treatment of cancers.

The methods of the invention will inevitably give rise to some cell killing by virtue of the photochemical treatment i.e. through the action of the photosensitizing agent. However, this cell death will not matter and may indeed be advantageous for many of the applications, e.g. cancer treatment, and may in some cases enhance the therapeutic effect by stimulating a local immune response. However, the methods of the invention may be modified such that the fraction or proportion of the surviving cells is regulated by selecting the light dose in relation to the concentration of the photosensitising agent. Again, such techniques are known in the art. Regardless of the amount of cell death induced by the pure photochemical treatment, it is important that the light dose is regulated such that some of the individual cells wherein the PCI effect is manifested are not killed by pure photochemical treatment (although they may subsequently be killed due to the PCI effect).

In some applications it may be appropriate to retain a larger number of viable cells after PCI treatment. For example in some gene therapy methods the amount of viable cells which allow for expression of the protein encoded by the transferred nucleic acid molecule is important. In such applications it is appropriate that a population or plurality of cells, substantially all of the cells, or a significant majority (e.g. at least 50%, more preferably at least 60, 70, 80 or 90% of the cells) are not killed. This of course is not always desirable especially when PCI is used to introduce cytotoxic transfer molecules and further cell killing is not disadvantageous. Cytotoxic effects may also however be achieved by using for example gene therapy in which a therapeutic gene is internalized into tumour cells by the method of the invention e.g. so that these cells will produce immunologically active substances that will induce local immunological killing of remaining cancer cells or induce a systemic immune response to the tumour cells. In such cases, clearly after PCI treatment a proportion of viable cells are required.

The advantages associated with PCI methods of internalisation of transfer molecules in association with viral carriers are 1) there is no restriction on the size of the molecule to be introduced into a cell as long as the molecule can be incorporated into a viral carrier and its viral carrier can be taken up by the target cell; 2) the methods are site specific in that only areas exposed to light are affected; 3) the internalisation of viral carriers is more efficient than standard viral infection in terms of the proportion of cells in which the transfer molecule is introduced and/or the level of expression of the transfer molecule; 4) lower doses and titres of virus are required because of the increased efficiency of internalisation; 5) it is not oncogenic.

The embodiments wherein the transfer molecule (and its viral carrier) is added to the cells after the light irradiation step have the further advantages that a) photochemical damage to the transfer molecule and its viral carrier is diminished;

b) simplification of PCI treatment of internal lesions in combination with surgery since photochemical treatment may be performed after surgical exposure of the lesion followed by e.g. intratumoral injection or other local administration of the viral carrier (and its associated transfer molecule);

c) the methods are more independent of exact timing of treatment, i.e. the timing of the addition of the molecule to be taken up by the cells relative to the time point of illumination. This means that there is a greater "time window" for treatment. This is important since uptake of a therapeutic molecule can vary widely in different clinical situations and moreover, the uptake is difficult to estimate for individual lesions in a clinical situation, therefore making a greater time window extremely advantageous;

d) rapid translocation of the transfer molecule to the cytosol occurs thereby substantially decreasing the possibilities for lysosomal degradation of the transfer molecule.

The methods of the present invention can be used to introduce molecules into cells as an alternative to prior art techniques of liposome fusion, calcium phosphate transfection etc. as discussed above.

In a preferred embodiment of the invention molecules are introduced into cells for the purposes of gene therapy.

Gene therapy may take place via a number of strategies, the most appropriate of which can be selected by a person skilled in the art depending on the particular pathogenesis of a disease.

One approach involves the targeted killing of specific cells. This approach is popular in cancer therapies and involves genes being directed to target cells and then expressed so as to cause cell killing. Such cell killing can take place by a direct mechanism, e.g. if the genes which are introduced encode a lethal toxin or encode a pro-drug which confers susceptibility on the cells to killing by a subsequently administered drug. Alternatively the cell killing can be indirect, e.g. by using immunostimulatory genes as the introduced genes in order to provoke or enhance an immune response against the target cell, or by using genes which encode a protein which causes cell death by interaction with an exogenously added molecule, (e.g. a gene encoding an enzyme that activates a pro-drug such as HSV-tk which activated GCV). Appropriate suicide genes, pro-drug encoding genes and immunostimulatory genes are well known and documented in the art.

A further approach involves targeted inhibition of gene expression. A variety of different techniques to specifically block the expression of a gene at the DNA, RNA or protein level are well known to a person skilled in the art, and any of these may be used in conjunction with the methods of the present invention, which can be used to introduce the appropriate molecular tools to block gene expression into the cells. Thus, in preferred aspects of the invention the molecule to be introduced is a DNA sequence comprising or capable of transcribing or expressing a functional product that will inhibit gene expression at some level in the target cells, e.g. by comprising, expressing or transcribing antisense molecules, ribozymes or intracellular antibodies.

Another approach involves gene augmentation therapy, when a disease state is caused by loss of function of a gene, and the diseases may be cured by introducing extra copies of the normal gene into appropriate cells of a patient. Thus in a further preferred feature of the invention, the molecule to be introduced is a gene or a portion thereof capable of expressing a functional product to compensate for a deficiency in a patient.

A yet further approach is that of targeted mutation correction, where the introduction of a nucleic acid into the appropriate cells of a patient leads to the direct correction of a disease-causing mutation in the patient's DNA. Methods for doing this are well known and described in the art.

Following nucleic acid/gene transfer into cells in accordance with the methods of the present invention, the inserted genes/nucleic acids may integrate into the chromosomes of the host cell, or remain as extra-chromosomal genetic elements (i.e remain episomal). Appropriate vectors can be chosen and designed to induce either of these possibilities.

The advantage of the introduced gene integrating into a chromosome is that the gene can be perpetuated by chromosomal replication following cell division. As progeny cells also contain the introduced genes, long-term stable expression of the introduced gene may be obtained. As a result, gene therapy using this approach may provide the possibility of a cure for some disorders. For example, in tissues composed of actively dividing cells, the aim may be to target the stem cells (a minority population of undifferentiated precursor cells which give rise to the mature differentiated cells of the tissue). Chromosomal integration has its disadvantages, however, which are well described and include e.g. the danger of cancer development for example due to an accidental integration event leading to the activation of an oncogene.

Ex vivo gene therapy, wherein the target cells are removed from a patient, manipulated in vitro and then reintroduced to a patient, offers the opportunity for selecting cells where integration has been successful. For example, by amplifying the cells in vitro and then checking the phenotypes for any obvious evidence of neoplastic transformation, prior to transferring the cells back into the patient. Ex vivo therapy may thus be preferred when chromosomal integration is desired.

Alternatively the vector system incorporating the gene/nucleic acid to be introduced may be designed to introduce genes into cells where they remain as extrachromosomal elements and can be expressed at high levels. If the cells are actively dividing, the introduced gene may not segregate equally to daughter cells and so long-term expression may be a problem. As a result, repeated treatments involving gene transfer may be necessary to effect a cure for a genetic disorder. The possibility of carrying out repeated treatments in this regard is however much increased with the present PCI based methods of transfer which allow higher efficiency targeted transfer of genes (see below). In addition, in some cases there may be no need for stable long-term expression. For example, cancer gene therapies often involve transfer and expression of genes into cancer cells with a view to killing the cells. In such methods, once the malignancy has been eliminated, the therapeutic gene is unlikely to be needed.

As mentioned above appropriate viral systems for use in the present invention are adenoviruses and adeno-associated viruses, retroviruses, lentiviruses, Herpes viruses, Sendai virus, bacteriophages, Vaccinia virus and Baculovirus.

Retroviruses have the advantageous property of being able to integrate into the chromosomal DNA but only infect actively dividing cells. The integrated DNA can be stably propagated, offering the possibility of a permanent cure for a disease. Their property of only infecting actively dividing cells, although disadvantageous for the treatment of many diseases is, however, beneficial to gene therapy for cancers of tissues that normally have non-dividing cells as the actively dividing cancer cells can be selectively infected and killed without major risk to the nondividing cells of the normal tissue.

Adeno-associated viruses require co-infection with a helper virus such as adenovirus or HSV for productive infection, i.e. infection which results in the production of progeny virions. However, in the absence of helper viruses chromosomal integration of the DNA can still take place. Thus, the appropriate type of adeno-associated virus vector can be selected depending on the application concerned.

Adenoviruses on the other hand infect also non-dividing cells. Entry into cells occurs by receptor-mediated endocytosis, but although the inserted nucleic acid migrates to the nucleus it does not appear to integrate and so expression of inserted genes can only be sustained over short periods. Adenovirus vectors can be produced at very high titres, and typically accept insert sizes of up to 7-8 kb, but recent developments in adenovirus vector technology allows the use of insert sizes up to about 30 kb in specially designed vectors (Kochanek (1999), Hum. Gene Ther. 10, 2451-2459). Because of their ability to infect many different types of cell, adenoviruses have found widespread applications, and are popular vectors for use in in vivo gene therapy strategies. Indeed, adenoviruses are the preferred viral carriers for use in the methods of the present invention.

However, although adenoviruses are among the most efficient vectors for in vivo gene delivery, their use is complicated by several serious problems, e.g. immunological reactions to the virus, transient gene expression and bad tissue distribution leading to low transduction efficiency in target tissues. Also the ability to restrict the expression of adenovirus-delivered therapeutic genes to target cells is difficult but may be very important to avoid adverse side effects, for example due to the expression of a toxic gene product (e.g. meant to kill cancer cells) in normal cells in the body, e.g. in vital organs such as the liver. Other viral carriers for use in gene therapy have similar drawbacks.

The use of photochemical internalisation in conjunction with the methods of the present invention can improve several of these issues. Firstly, the use of PCI can substantially increase the level and extent of transgene expression in target tissues (i.e. can lead to a greater number of cells expressing higher levels of the transgene). In addition, PCI has been shown to increase the efficiency of viral infection such that a significantly lower viral dose is required to produce the same amount of gene transduction seen in the absence of PCT. This efficiency of PCI enhanced viral infection at lower multiplicity of infection values (MOIs) should allow viral transduction in areas of tissue which have low virus penetration, thereby allowing transduction in regions receiving too few virus particles to be effectively transduced with conventional infection. Since it is expected that with local administration virus concentration in tissues will drop rapidly with increased distance from the application point this is a very important improvement of viral infection technology.

A further advantage of the PCI induced increased efficiency of viral infection is that a lower virus dose can be used while maintaining transduction efficiency thereby reducing immunological problems associated with adenovirus and other virus mediated gene therapy. Finally, the photochemical treatment can be used to increase the specificity of infection to the target cells. This is firstly because only illuminated areas are subjected to PCI and secondly because some photosensitizers inherently accumulate preferentially in diseased areas. The ability to direct the activity of a therapeutic gene to a site of disease simply by shining light on the diseased area is a very favourable aspect of the present invention, which to a high degree should make it possible to avoid unwanted side effects due to the expression of the therapeutic gene at the "wrong" places in the body. The ability of PCI to make possible the use of lower doses of the gene therapeutic agent will also contribute to lessen the side effects. The specificity which is obtainable is expected to make systemic administration of adenovirus and other viral carriers feasible. Furthermore, as discussed above PCI could also be combined with targeted vectors, potentially further improving gene delivery specificity.

As discussed in the previous PCI applications it is believed that the transfection-enhancing effect of PCI on plasmid/polylysine complexes and the enhancing effect on the delivery of other molecules such as proteins, is due to a light-induced rupture of endocytic vesicles, and, whilst not wishing to be bound by theory, it seems reasonable that the same mechanism should be involved in the stimulation of adenovirus-mediated gene transduction. However, in contrast to plasmid/polylysine complexes and other molecules such as proteins, the escape of adenovirus from endosomes is believed to be an efficient process, where more than 40% of the cell bound virus particles have been reported to reach the cell nucleus (Greber, U. F. et al. (1993), Cell 75, 477-486; Leopold, P. L. et al. (1998), Hum. Gene Ther. 9, 367-378). Thus, from what is described in the literature one would have expected that PCI at most could increase the efficiency of adenovirus gene transduction 2.5 times if PCI was able to induce the nuclear transport of all the cell bound virus particles. It was therefore extremely surprising that PCI-induced enhancements in gene transduction of more than 20 times could be observed, and at present we have no good explanation for this unexpectedly large effect. One possibility is that virus particles subjected to PCI may have a higher "inherent transduction efficiency" than viruses in normal infection, e.g. due to a different release mechanism from the endosomes. It is also possible that endosomal release of adenovirus in normal infection is less efficient at the low MOIs (multiplicity of infection) where PCI has the best effect. It is also possible that the photochemical treatment may affect other processes such as virus uptake, nuclear transport or transcription of the transgene.

In a further aspect the present invention provides pharmaceutical compositions comprising a transfer molecule associated with a viral carrier and a photosensitizing agent, preferably for use in therapy. Optionally the photosensitizing agent in the compositions may also be associated with viral carrier molecules or other non-viral carrier molecules such as those described above. Preferably the viral carrier is itself attached to, associated with, or conjugated to, one or more carrier molecules (preferably polycations or cationic lipids), targeting molecules or targeting vectors. Optionally one or both of the viral carrier and the photosensitizing agent may be associated with the same or different targeting molecules as described above. Preferably the compositions are for use in gene therapy. For gene therapy a preferred viral carrier molecule is adenovirus or a viral carrier derived therefrom. Conditions, diseases and infections which are particularly suitable for gene therapy include cancerous tumours e.g. basal cell carcinomas, dysplasia or other growths, rheumatoid arthritis, artherosclerosis, virus and other infections, psoriasis, solar keratosis, wound healing, fracture healing, warts and inherited genetic disorders such as cystic fibrosis, Gorlin's syndrome, ataxia telangiectasia and metabolic disorders.

Preferred genes to be used as transfer molecules for gene therapy are genes encoding prodrug activating enzymes such as Herpes Simplex thymidine kinase or cytosine deaminase; protein toxins such as diphteria toxin or gelonin, apoptosis inducing proteins such as p53 or apopoptin; immune stimulating factors such as interleukins (IL-2, IL-12, IL-18 preferred), tumor necrosis factor α, chemokines; tumor specific antigens such as mutated ras proteins or Mart-1; immune/inflammation inhibitors such as interleukin-10, IL-1 receptor antagonist or soluble TNF-receptor; angiogenesis inhibitors such as endostatin; proteins inducing vessel formation such as vascular endothelial growth factor; coagulation initiating proteins such as tissue factor; intracellular antibodies; recombinant immunotoxins; ribozymes or antisense RNA molecules and so on.

In a further aspect therefore the present invention provides the use of a transfer molecule associated with a viral carrier and a photosensitizing agent as described herein for the preparation of a medicament for use in therapy, preferably gene therapy. For said uses, the photosensitizing agent and the viral associated transfer molecule is contacted with cells or tissues of a patient either together or separately by selecting appropriate administration times and said cells are irradiated as described above with light of a wavelength effective to activate the photosensitizing agent.

Methods of treatment and preferably methods of gene therapy comprising the methods of the invention form alternative aspects of the invention. Thus, the invention provides a method of treating or preventing a disease, disorder or infection in a patient by gene therapy comprising introducing a transfer molecule into one or more cells in vitro, in vivo or ex vivo according to the method as described hereinbefore and where necessary (ie. when transfection is conducted in vitro or ex vivo) administering said cells to said patient.

As defined herein "treatment" refers to reducing, alleviating or eliminating one or more symptoms of the disease, disorder or infection which is being treated, relative to the symptoms prior to treatment. "Prevention" refers to delaying or preventing the onset of the symptoms of the disease, disorder or infection.

Compositions of the present invention may also comprise a cell or a population of cells containing a transfer molecule which has been introduced into said cell by the methods of the invention, preferably for use in therapy, particularly gene therapy.

Thus, a yet further aspect of the invention provides a cell or a population of cells containing a transfer molecule which has been introduced into said cell, which cell is obtainable by a method of the present invention.

A yet further aspect of the invention provides the use of a such a cell or population of cells for the preparation of a composition or a medicament for use in therapy, preferably gene therapy.

The invention further provides a method of treatment of a patient comprising administering to said patient cells or compositions of the present invention.

Preferably said methods are used in gene therapy, ie. a method comprising the steps of introducing a molecule into a cell as described hereinbefore and administering said cell thus prepared to said patient.

In vivo, any mode of administration of the viral carriers, photosensitizing agents, cells containing transfer molecules, compositions etc., common or standard in the art may be used, e.g. intramuscular, sub-cutaneous, intraperitoneal, intratumoral or intravenous injection, infusion, inhalation or topical administration, both to internal and external body surfaces etc. For in vivo use, the invention can be used in relation to any tissue which contains the cells to which the photosensitising agent and the viral carrier will localise, including body fluid locations, as well as solid tissues. All tissues can be treated as long as the photosensitiser is taken up by the target cells, and the light can be properly delivered. With regard to light delivery, clearly this does not present a problem for external surfaces of the human or animal body. For internal surfaces techniques such as for example the use of optical fibre devices can be used to effectively illuminate many internal surfaces. In addition, the treatment can be done in combination with surgery that will expose surfaces which need to be treated.

Thus, the compositions of the invention may be formulated in any convenient manner according to techniques and procedures known in the pharmaceutical art, e.g. using one or more pharmaceutically acceptable carrier or excipients (i.e. compatible with other ingredients in the composition as well as physiologically acceptable to the recipient). The nature of the composition and carriers or excipient materials, dosages etc. may be selected in routine manner according to choice and the desired route of administration, purpose of treatment etc. The compositions of the invention may also contain other appropriate agents. For example, for some therapeutic applications and some routes of administration it may be beneficial to use for example agents that can increase tissue penetration of the viral carrier, e.g. proteases (Kuriyama, N. et al., 2000, Hum. Gene. Ther. 11: 2219-2230).

Compositions may be administered topically (e.g. by intestinal, buccal, sublingual, gingival, palatal, nasal, pulmonary, vaginal, rectal or ocular delivery), orally or parenterally. Topical compositions are preferred, and include gels, creams, ointments, sprays, lotions, salves, sticks, soaps, powders, tablets, films, pessaries, aerosols, drops, solutions and any of the other conventional pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

The compositions may additionally include lubricating agents, wetting agents, emulsifying agents, suspending agents, preserving agents, sweetening agents, flavouring agents, adsorption enhancers, e.g. surface penetrating agents as mentioned below, and the like. The compositions of the invention may be formulated so as to provide quick, sustained or delayed release of the active ingredient after administration of the patient by employing procedures well known in the art. Solubilizing and/or stabilizing agents may also be used, e.g. cyclodextrins (CD) α, β, γ and HP-β cyclodextrin.

Dosages may likewise be determined in routine manner and may depend upon the nature of the molecule, purpose of treatment, age of patient, mode of administration etc. In connection with the photosensitizing agent the potency/ability to disrupt membranes on irradiation, should also be taken into account. Generally however, for in vitro use a concentration range for the photosensitizer of e.g. 0.05-500 µg/ml is suitable. For human in vivo treatments the photosensitizing agent may be used in the range 0.05-20 mg/kg body weight when administered systemically or 0.1-20% in a solvent for topical application. In smaller animals the concentration range may be different and can be adjusted accordingly.

The molecule to be introduced in association with the viral carrier may be present at a concentration of $1\times10^{-9}$ to 50% such as $3\times10^{-6}$ to 50%, e.g. 0.003 to 30%, e.g. 0.2 to 10% (w/w) of virus particles in the final composition for use in vivo in which w/w refers to the weight of the viral carrier in addition to the molecule to be introduced relative to the weight of the final composition. If used in 1 ml injections, this would correspond to a dose of approximately $10^5$ to $10^{15}$ physical viral particles. For in vitro use between $1-1\times10^5$ viral particles, e.g. $1\times10^3-1\times10^5$, may be used.

BRIEF DESCRIPTION OF THE DRAWINGS

The invention will now be described in more detail in the following non-limiting Examples with reference to the following drawings in which.

After 2 days incubation to allow for expression of the transduced β-galactosidase gene the cells were stained with X-gal and analyzed by microscopy as described. The cells were treated as follows: A. No treatment. B. Adenovirus only. C. $AlPcS_{2a}$+8 min light. D $AlPcS_{2a}$+Adenovirus+8 min light.

Figure 2A:
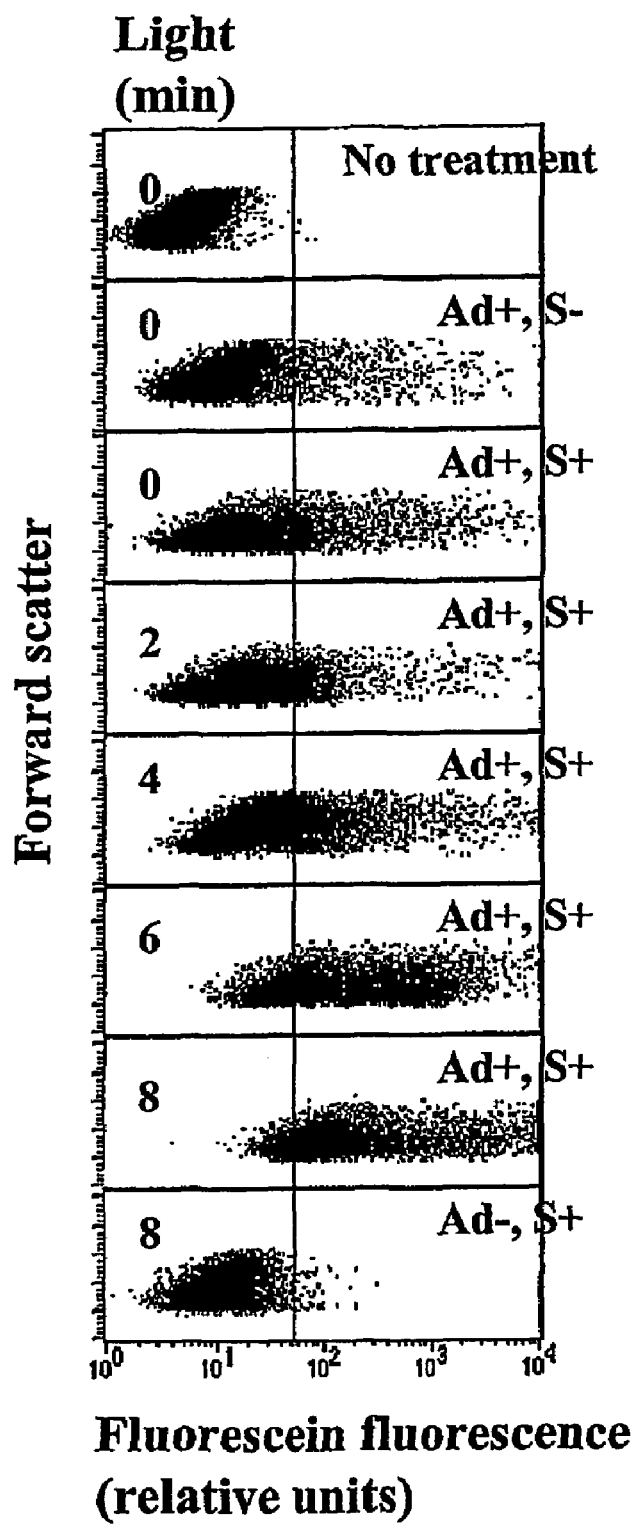

FIG. 2 shows flow cytometry analysis of photochemically enhanced transduction in HCT 116 (panel A) and WiDr (panel B) cells. The cells were treated with $AlPcS_{2a}(S)$, infected with AdHCMV-lacZ(Ad) at MOI5 and illuminated as described. Two days later the cells were loaded with fluorescein di-β-D-galactopyranoside and analysed by flow cytometry. FIG. 2A shows a dot plot of the flow cytometry analysis of HCT 116 cells.

Figure 2B:
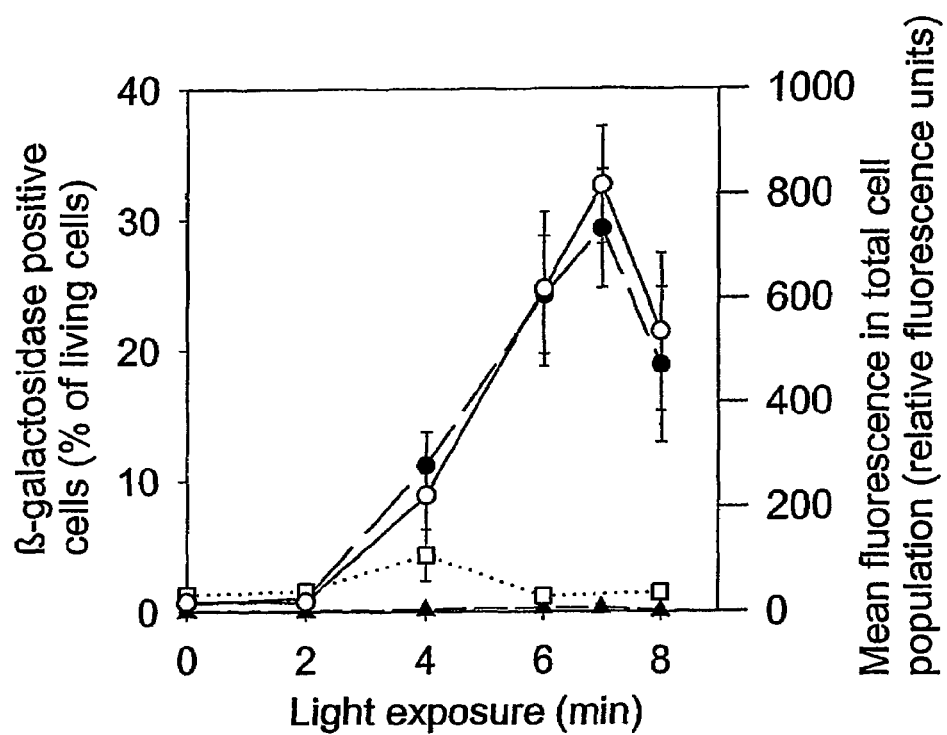

The cells on the right side of the vertical line were considered as positive for adenovirus transduction since there were virtually no cells in this area either for nontreated cells (upper panel), or for cells receiving only $AlPcS_{2a}$ and light (lower panel). The different treatments are indicated in each panel. FIG. 2B shows transduction-efficiency as a function of light dose for WiDr cells. % β-galactosidase positive cells defined as described under FIG. 2A (($\square$) S−, Ad+; (▲) S+, Ad−; (•) S+, Ad+) and mean fluorescence intensity (($\bigcirc$) S+, Ad+) was scored. The bars represent standard error of the mean (SEM) of 2 to 5 different experiments.

Figure 3A:
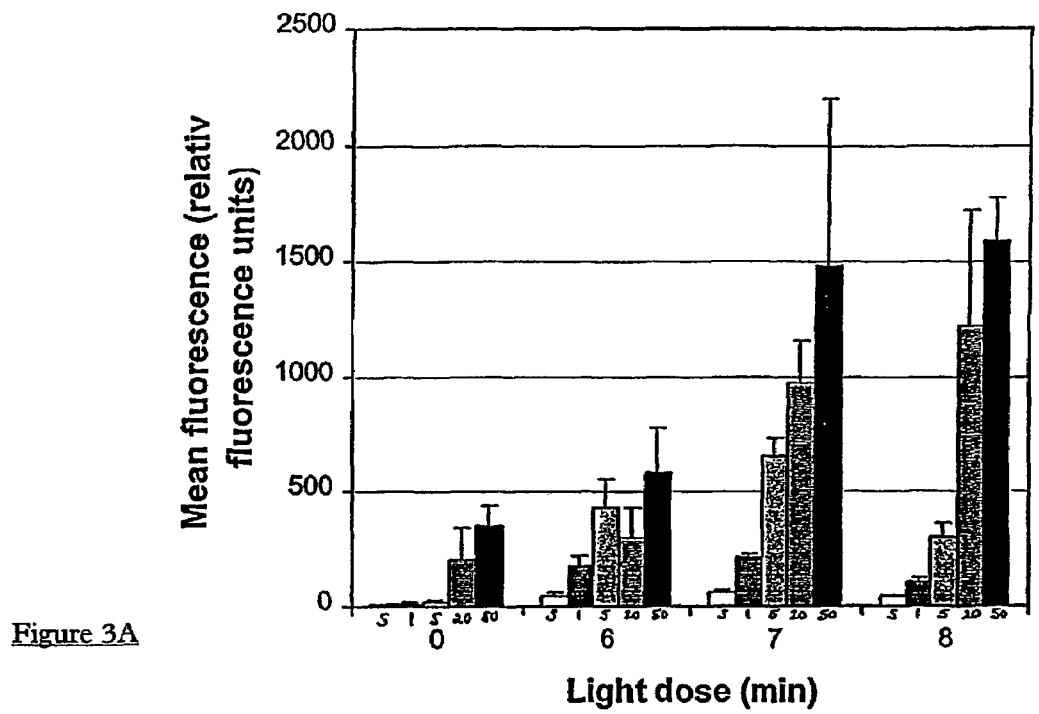
Figure 3B:
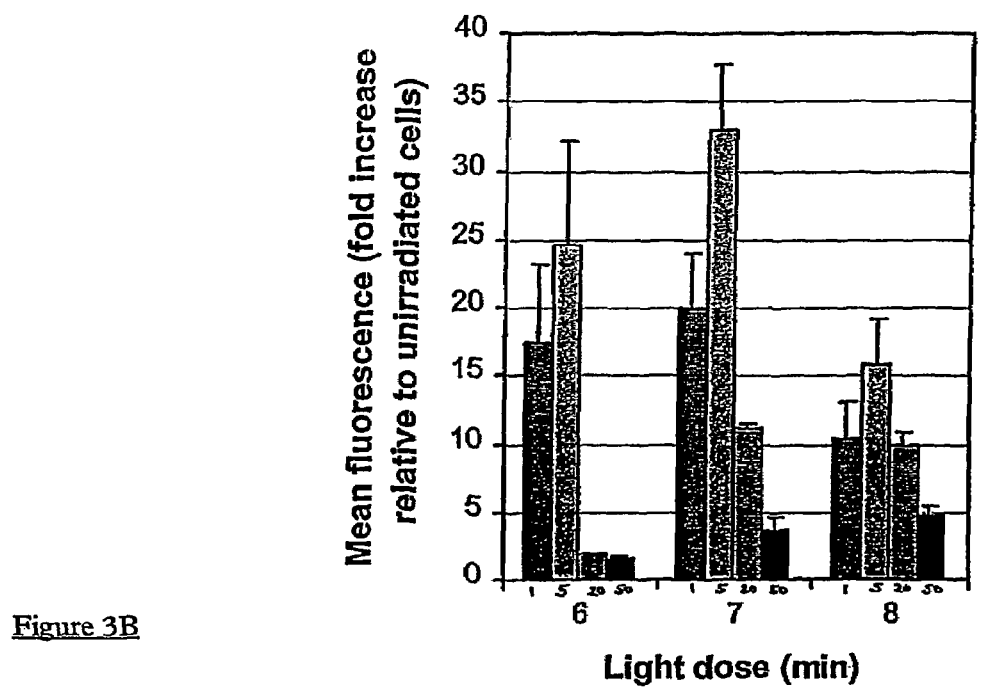

FIG. 3 shows PCI-enhanced transduction of WiDr cells at different virus doses. The cells were infected with AdHCMV-lacZ at different MOIs and subjected to photochemical treatment as described. FIG. 3A shows mean fluorescence of the total cell population. Treatments were as follows: Unshaded bars: only $AlPcS_{2a}$; diagonal cross-hatch: MOI=1; grey: MOI=5; horizontal cross-hatched: MOI=20; black: MOI=50. Error bars are SEM of 3 experiments. FIG. 3B shows fold increase in β-galactosidase activity of the total cell population. Symbols are the same as in FIG. 3A. Error bars are standard error of 3 or 4 experiments.

Figure 4:
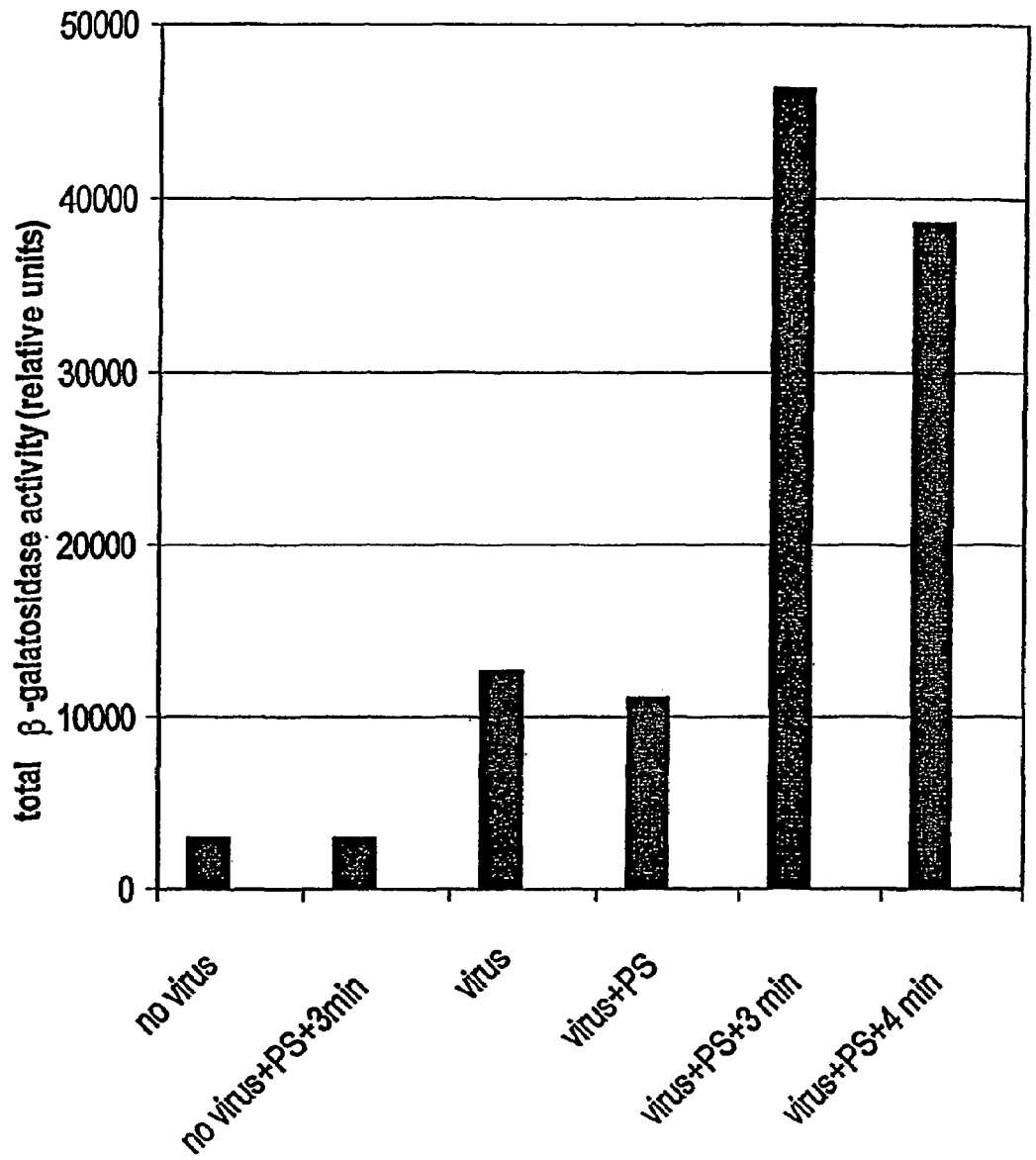

FIG. 4 shows the effect of photochemical treatment on adenovirus transduction of THX cells.

Figure 5:
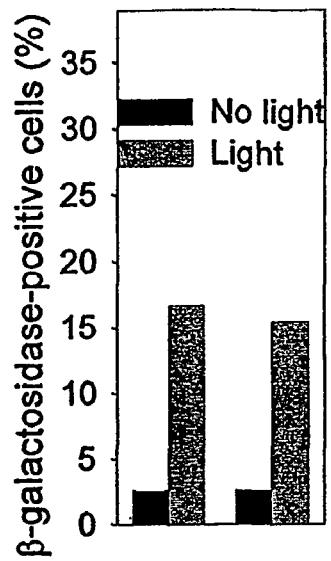

FIG. 5 shows the effect of photochemical treatment on expression of β-galactosidase in THX cells infected with AdHCMV-lacZ. For the "light before" strategy $AlPcS_{2a}$-pretreated cells were incubated for another 4 h in $AlPcS_{2a}$-free medium before light exposure for 3 min. Following illumination the cells were infected with AdHCMV-lacZ (at MOI 1)

for 30 min at 37° C. Then 2 ml of medium was added and the cells were incubated for two days before analysis of β-galactosidase expression. For the "light after" strategy AlPcS$_{2a}$-treated cells were incubated in AlPcS$_{2a}$-free medium for 3 h before a 30 min infection with AdHCMV-lacZ. After addition of 2 ml of culture medium the cells were incubated for another 30 min before illumination for 3 min, and two days later were analysed for β-galactosidase expression.

Figure 6:
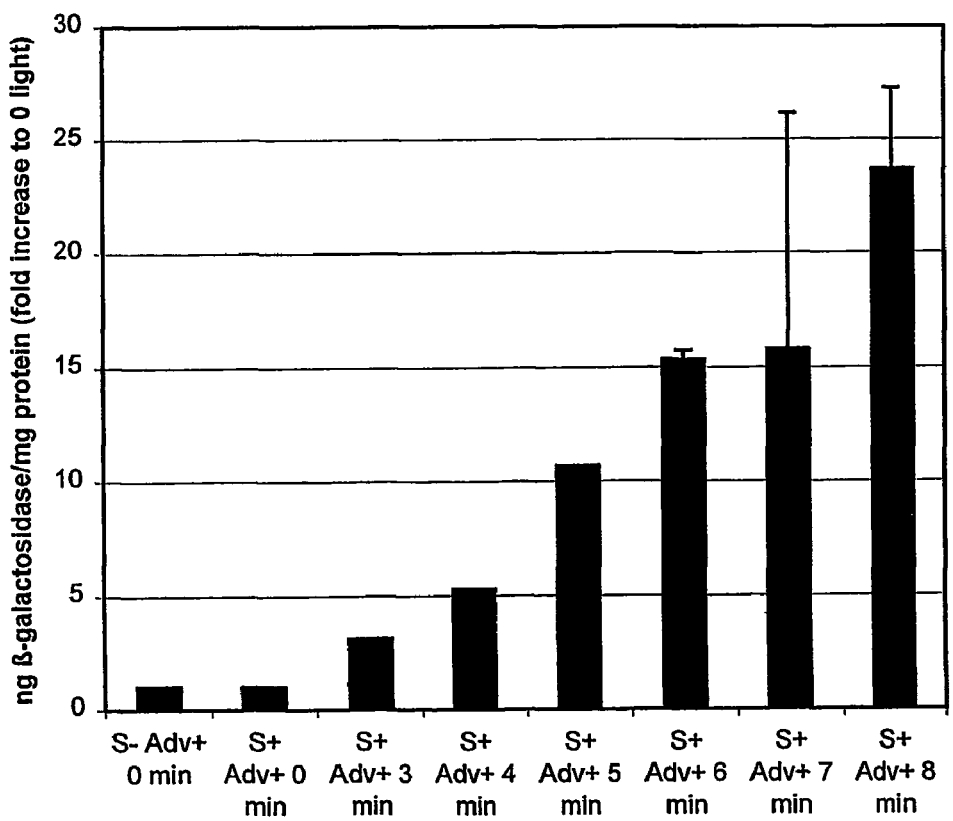

FIG. 6 shows the increase in β-galactosidase production as a result of PCI-mediated transduction with an adenovirus encoding β-galactosidase with increasing irradiation times. The treatment (+,− indicating with or without) and light doses (length of irradiation) for the different samples are indicated on the figure. Adv: Adenovirus AdHCMV-LacZ. S: the photosensitizer AlPcS$_{2a}$.

Figure 7:
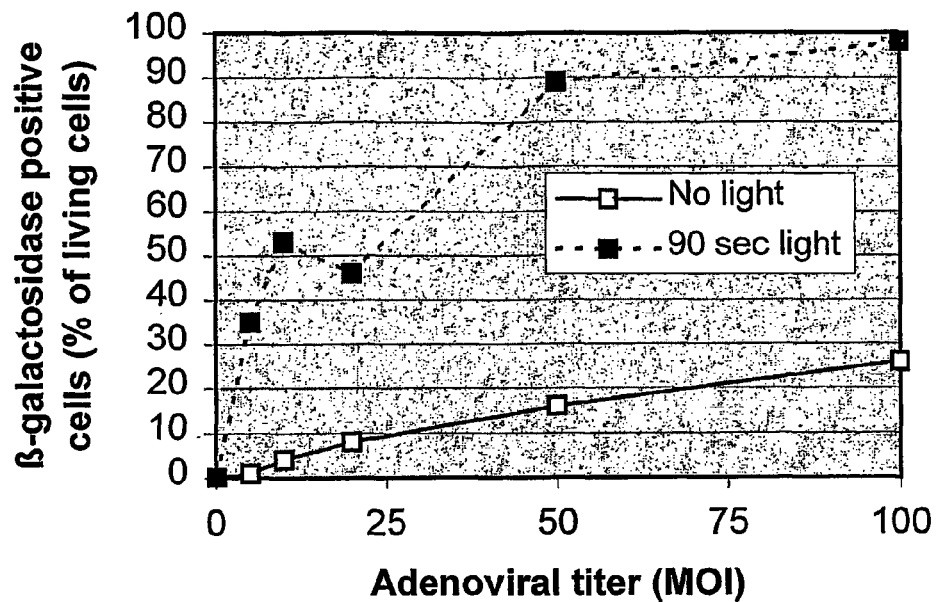

FIG. 7 shows the effect of PCI on transduction of WiDr cells at different multiplicities of infection. □-without irradiation, ■-90 seconds irradiation.

Figure 8:
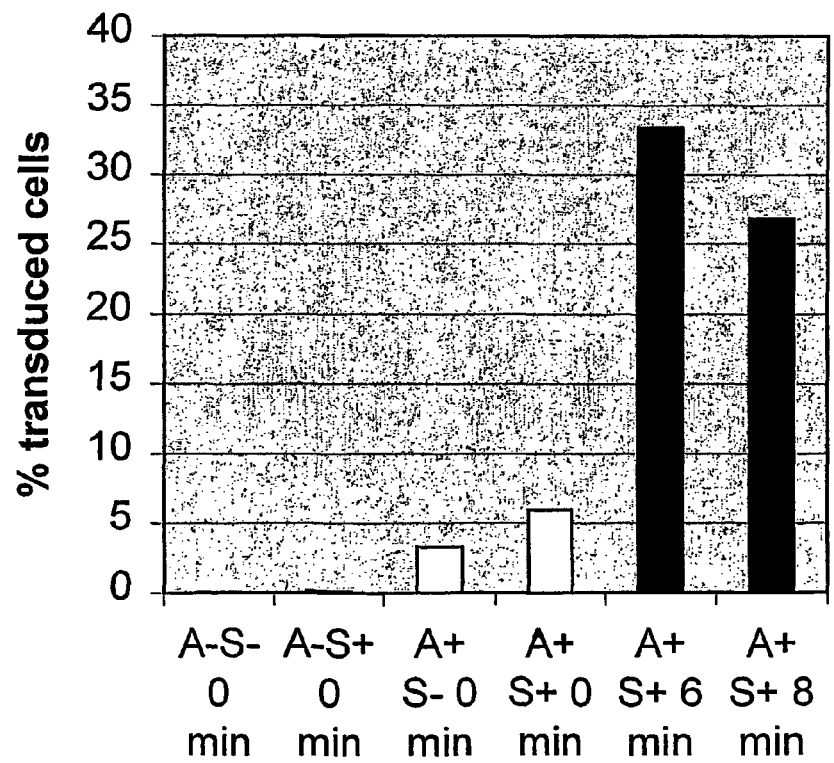

FIG. 8 shows the effect of PCI on adenovirus transduction of A549 cells. The treatment (+,− indicating with or without) and light doses (in minutes) for the different samples are indicated on the figure. A: Adenovirus AdHCMV-LacZ. S: the photosensitizer AlPcS$_{2a}$.

Figure 9:
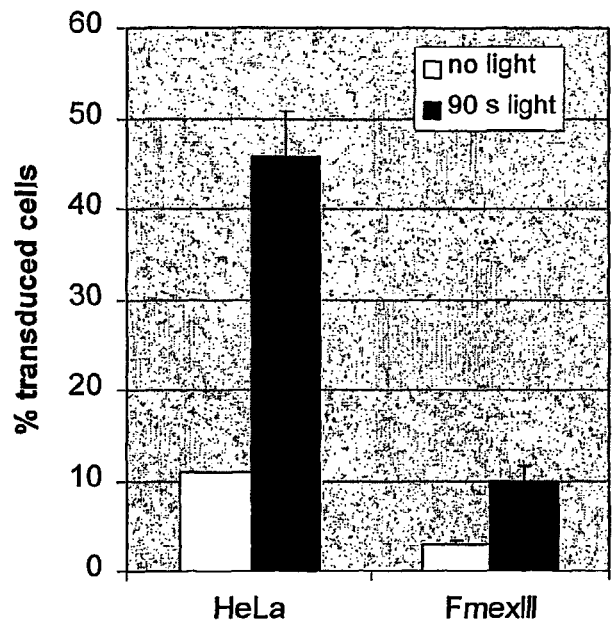

FIG. 9 shows the PCI effect on transduction of HeLa and FinexIII cell lines. Unshaded bars—no irradiation, solid bars—90 seconds irradiation.

Figure 10:
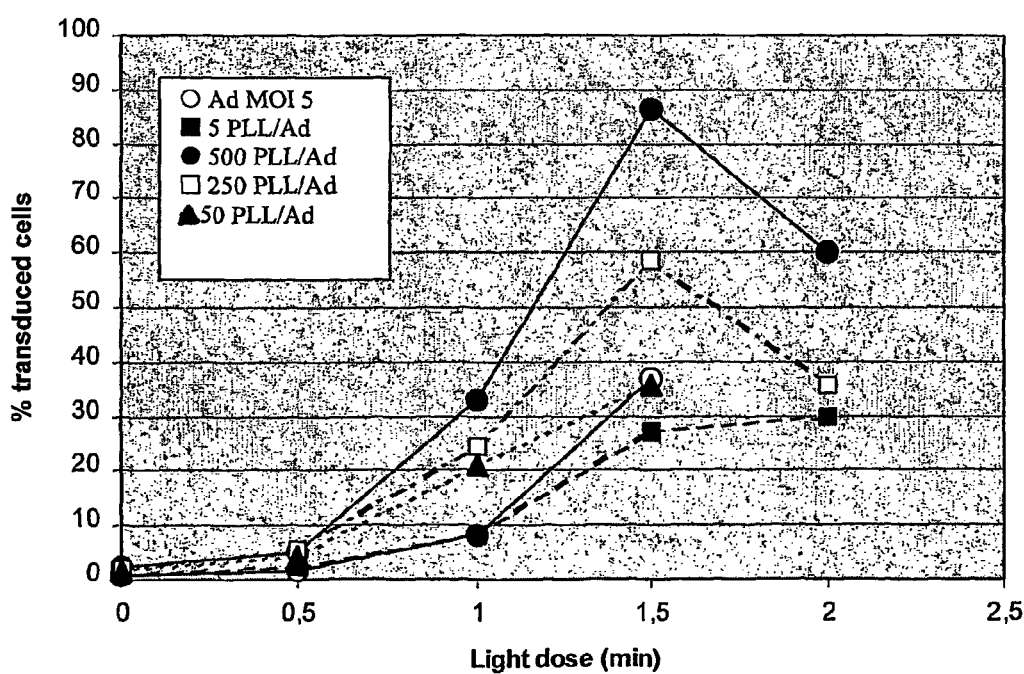

FIG. 10 shows the effect of PCI on transduction of WiDr cells with adenovirus associated with a poly-L-lysine carrier. Ad: Adenovirus AdHCMV-LacZ. PLL: Poly-L-Lysine. 5PLL/Ad means that the complex on average contains 5 PLL molecules per virus particle. ○—Ad MOI 5, ■—5 PLL/Ad, •—500 PLL/Ad, □—250 PLL/Ad, ▲—50 PLL/Ad.

Figure 11:
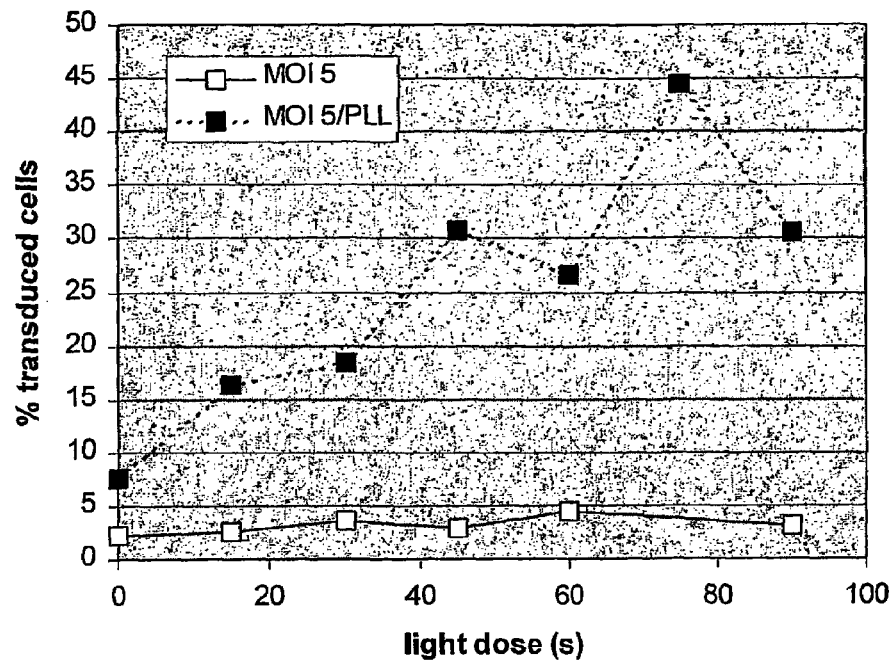

FIG. 11 shows the effect of PCI on adenovirus transduction of a human skin fibroblast cell line employing poly-L-lysine as a carrier for the virus with variable irradiation times. □—MOI 5: Uncomplexed adenovirus AdHCMV-LacZ. ■—MOI 5/PLL: AdHCMV-LacZ complexed to 250 molecules of PLL per virus particle.

Figure 12:
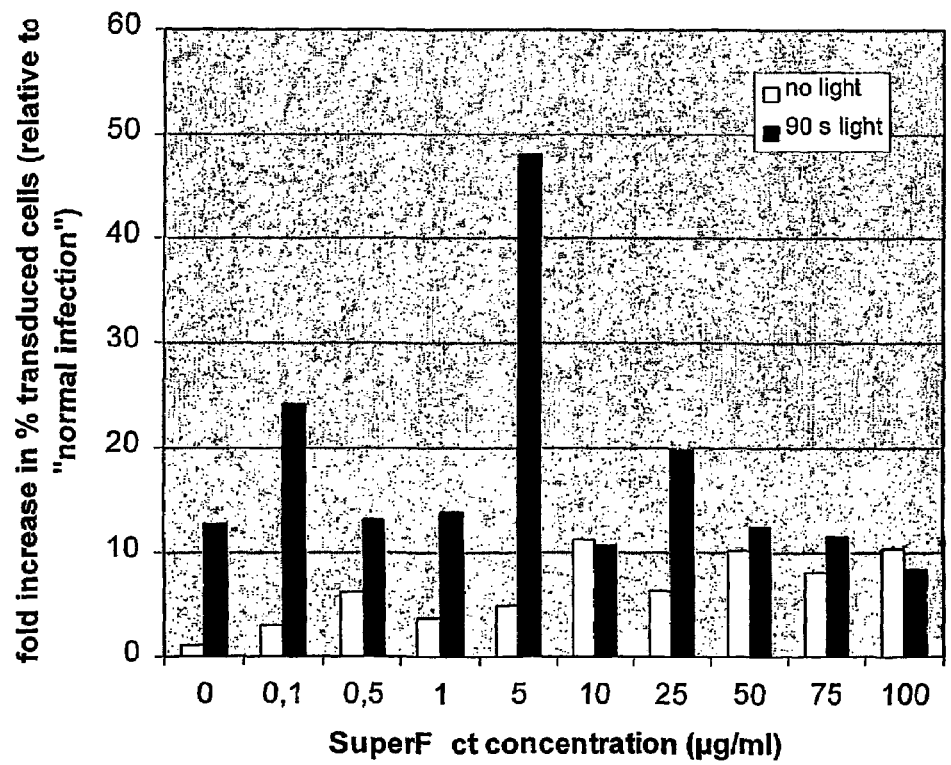

FIG. 12 shows the effect of PCI on adenovirus transduction using the polycationic dendrimer SuperFect® as a virus carrier at various concentrations. Unshaded bars—without irradiation, solid bars—90 seconds irradiation.

Figure 13:
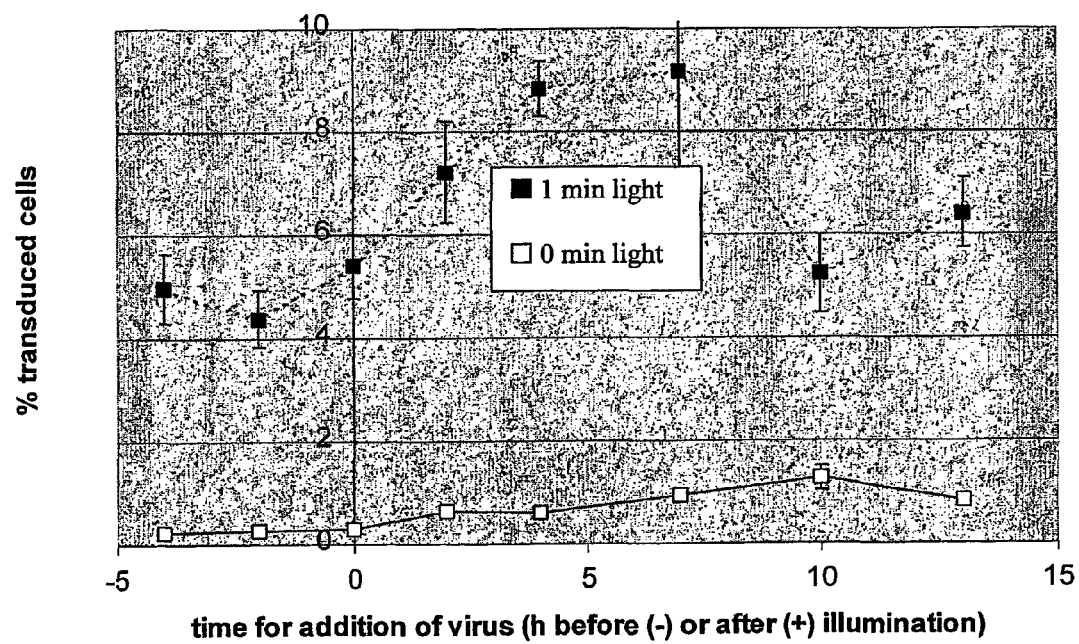

FIG. 13 shows the effect of different time schedules of illumination and administration of adenovirus. Time points to the left of the Y-axis represent virus added before irradiation, time points to the right represent addition of virus after irradiation. ■-1 minute irradiation; □—no irradiation.

Figure 14:
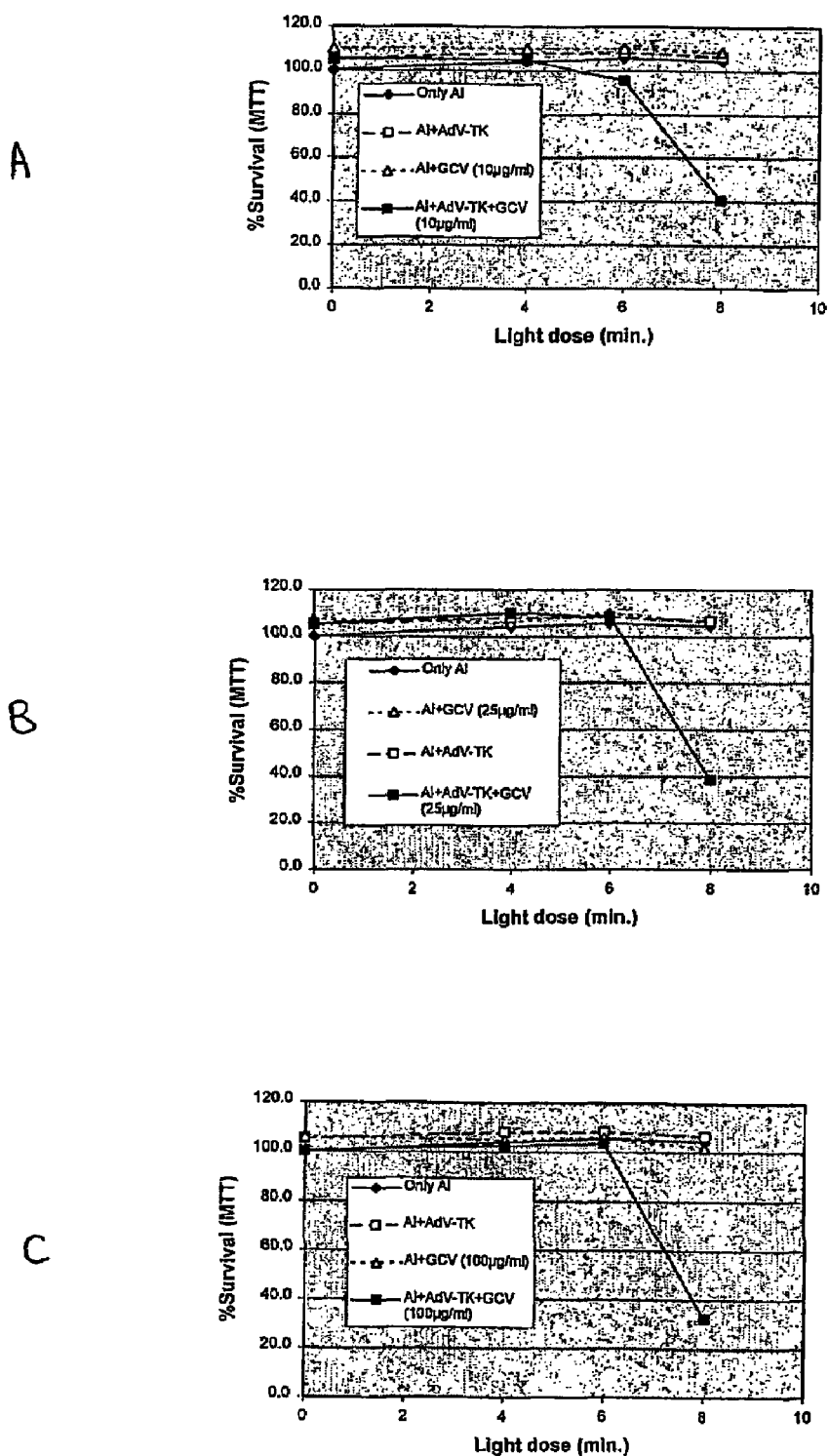

FIG. 14 shows PCI enhancement of the gene therapeutic effect of an adenovirus vector encoding Herpes Simplex Virus thymidine kinase after various irradiation times. Cell killing was effected by ganciclovir after PCI induced gene transduction with an adenovirus vector encoding HSV-tk. Al: AlPcS$_{2a}$; AdV-TK: Adenovirus encoding HSV-tk; GCV: ganciclovir. ♦—Al only; □—A1+AdV-TK; ▬—AL+GCV at 10 µg/ml (A), 25 µg/ml (B) or 100 µg/ml (C); ■-AL+AdV-TK+GCV at 10 µg/ml (A), 25 µg/ml (B) or 100 g/ml (C).

EXAMPLE 1

Figure 1:
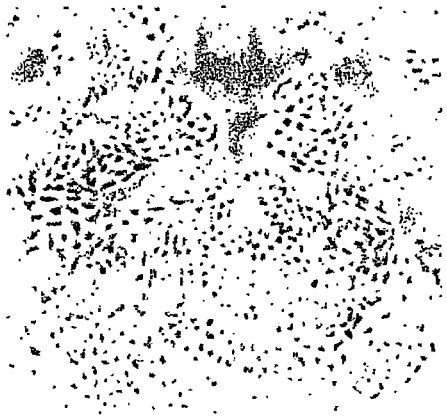
FIG. 1 shows X-gal staining of photochemically transduced WiDr cells. The cells were treated with $AlPcS_{2a}(S)$, infected with AdHCMV-lacZ (Ad) at MOI 5 and subjected to light treatment as indicated in the figure.
Figure 1:
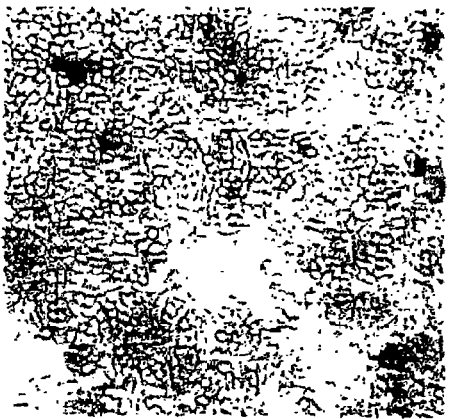
Figure 1:
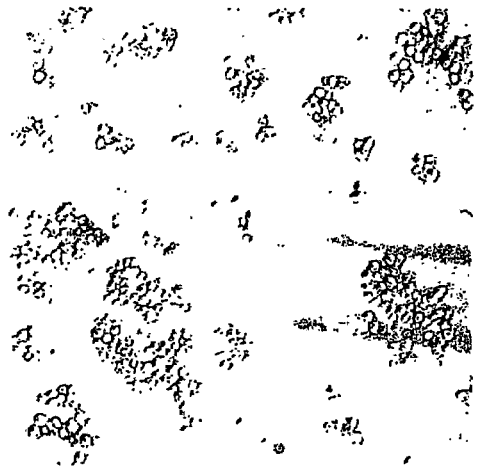
Figure 1:
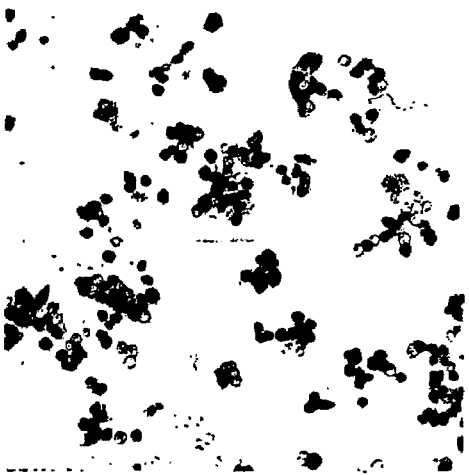

In initial experiments human WiDr adenocarcinoma cells were treated with the photosensitizer AlPcS$_{2a}$ (aluminum phthalocyanine with 2 sulfonate groups on adjacent rings), infected with the AdHCMV-lacZ adenovirus containing a β-galactosidase reporter gene and subjected to light treatment as described in Experimental protocol. The cells were stained for β-galactosidase activity, and microscopy showed that a substantial fraction of the light-treated cells expressed the transgene (FIG. 1D), while only a few positive cells were detected among nonilluminated adenovirus-infected cells (FIG. 1B). No positive cells were seen in untreated samples (FIG. 1A) or in samples receiving AlPcS$_{2a}$ and light, but no adenovirus (FIG. 1C), thus the observed light-induced increase in β-galactosidase expression originated from the adenovirus-delivered transgene, and not from an endogenous β-galactosidase gene.

EXAMPLE 2

For quantitative analysis flow cytometry was employed, using the substrate fluorescein di-β-D-galactopyranoside that makes β-galactosidase-expressing cells fluorescent. As can be seen from FIG. 2A the photochemical treatment substantially increased the β-galactosidase activity in adenovirus-infected HCT 116 cells. Thus, the percentage of β-galactosidase positive cells increased from 6.3±0.1% (standard deviation, n=3) in normally-infected cells (Ad+, S−, 0 min light) to 88±17% (n=3) in cells receiving optimal treatment (Ad+, S+, 8 min light). Likewise for the same samples the mean fluorescence intensity increased from 52±11% (n=3) to 632±163% (n=3) relative fluorescence units (RFU). The photochemical treatment also slightly increased the mean fluorescence in non-infected cells (FIG. 2A, upper and lower panels) from 6 to 12 RFU. However, because of the very low levels of fluorescence and positive cells (0.4% in the Ad−, S+, 8 min sample) this did not generate difficulties in interpreting the results for virus-infected cells.

In WiDr colon carcinoma cells even higher light-dependent increases in gene transduction was observed (FIG. 2B). Thus, maximally a 22-fold increase in the percentage of β-galactosidase positive cells and a 44-fold increase in the mean fluorescence intensity were found when illuminated virus-infected cells were compared to nonilluminated cells. Photochemical treatment alone (FIG. 2B, Ad−, S+, Δ) did not significantly change the percentage of positive cells, neither did illumination alone (FIG. 2B, Ad+, S−, □).

The flow cytometry results were confirmed by using the chemiluminescent β-Gal reporter gene assay kit (Roche, Cat. No. 1 758 241) on extracts from WiDr cells, showing a 30-fold increase in β-galactosidase activity as a result of the photochemical treatment (not shown).

EXAMPLE 3

We next studied the effect of the virus dose on the photochemically enhanced transduction efficiency. As is apparent from FIG. 3 the photochemical treatment increased transduction at all virus doses tested. However, the effect was more pronounced at the lower virus doses (MOIs (multiplicity of infection) 1 and 5) where increases in mean fluorescence of between 15- and 35-fold was observed, as compared to about 10- and 5-fold increases at MOIs 20 and 50, respectively (FIG. 3B). It can also be seen (FIG. 3A) that the mean fluorescence obtained at the optimal light dose (7 min) at MOI 5 is about twice the level observed without light treatment at MOI 50. Likewise the level achieved with light treatment at MOI 1 is about the same as for MOI 20 without light treatment. Thus, with optimal photochemical treatment a 20 times lower virus dose is sufficient to give the same level of gene transduction as for infection without photochemical treatment.

The percentage of β-galactosidase positive cells obtained at MOI 50 in this experiment was 90±3% (n=3) as compared to 13%±4 (n=3) for nonilluminated cells. Together with the results for HCT 116 cells presented above this indicates that with adenovirus PCI can transduce the total cell population.

Experimental Protocols.

Cells and Adenovirus.

HCT 116 and WiDr human colon carcinoma cells were obtained from American Type Culture Collection (ATCC nos. CCL-247 and CCL-218, respectively). Cells were cultured in RPMI 1640 medium containing 10% fetal calf serum, 100 U/ml penicillin, 100 mg/ml streptomycin and 2 mM glutamine (all Gibco BRL, Paisley, UK) at 37° C. in 5% $CO_2$ atmosphere.

The recombinant adenovirus AdHCMV-lacZ encoding the E. coli lacZ gene controlled by the human cytomegalovirus promoter was obtained by homologous recombination using the pJM17 system in 293 cells (Addison et al., 1997, J. Gen. Virol. 78: 1653-61). Recombinant vectors were plaque purified, grown to high titer in 293 cells and purified by CsCl banding (Hitt et al., 1995, Methods Mol. Genet. 7:13-30). The virus-solution was diluted in PBS containing 0.68 mM $CaCl_2$ and 0.5 mM $MgCl_2$ to the MOIs employed in the different experiments.

Photochemical Treatment.

50 000 cells per well were seeded in 6-well plates (Costar,) and incubated overnight at 37° C. 1 ml medium containing 20 mg/ml $AlPcS_{2a}$ (Phorphyrin Products, Logan, Utah) was added, the cells were incubated for 18 h at 37° C., washed three times with medium and incubated for another 3 h at 37° C. The medium was removed and 200 µl of AdHCMV-lacZ was added. After incubation for 30 min at 37° C., 2 ml medium was added and the cells were incubated for 30 min before exposure to red light (Phillips TL 20 W/09, filtered through a Cinemoid 35 filter, with a light intensity reaching the cells of 13.5 W/$m_2$). Before analysis of β-galactosidase activity the cells were incubated at 37° C. for two days.

X-Gal Staining of Cells

For X-gal (5-bromo-4 chloro 3 indolyl-β-D-galactopyranoside) staining the medium was discarded, 1 ml of fixative solution (0,05% glutaraldehyde in PBS) was added and the cells were incubated at room temperature for 15 min. The fixative solution was discarded and the cells were washed three times in PBS at room temperature (second rinse was for 10 min, first and third rinses were performed quickly). 1 ml X-gal solution (5 mM $K_3Fe(CN)_6$, 5 mM $K_4Fe(CN)_6$, 1 mM $MgCl_2$, 1 mg/ml X-gal) was added and the cells were incubated for 4 h to overnight at 37° C. and observed by microscopy (100× magnification) using an Axiovert S100 microscope (Zeiss) with an MC100 Spot camera (Zeiss).

Flow Cytometry Analysis

The cells were trypsinised, centrifuged, resuspended in 25 ml medium and incubated for 5 min at 37° C. 25 ml of 2 mM fluorescein di-β-D-galactopyranoside (Molecular Probes, Eugene, Oreg.) was added, and the cells were incubated for 1 min at 37° C. before being diluted by adding 450 ml ice cold growth medium. The samples were kept on ice for 30-60 min, filtered through a 50 mm mesh nylon filter and analyzed in a FACS-Calibur flow cytometer (Becton Dickinson). For each sample 10 000 events were collected. Fluorescein-fluorescence was measured through a 510-530 nm filter after excitation with an argon laser (15 mW, 488 nm). Dead cells were discriminated from single viable cells by gating on forward scattering versus side scattering. The data were analyzed with the CELLQuest Software (Becton Dickinson).

EXAMPLE 4

Effect of PCI on Adenovirus Transduction of THX Cells Material

Fluorescein di-β-D-galactopyranoside (FDG) was purchased from Molecular Probes (F-1179). A 20 mM stock solution was prepared by dissolving the powder in a 1:1 mixture of DMSO/ethanol. The mixture was gradually added to an appropriate volume ice-cold water to make a 8:1:1 $H_2O$/DMSO/ethanol solution.

The recombinant virus AdCA17lacZ was formed and propagated in the human cell line 293, an Ad E1-transformed embryonic kidney cell line maintained in MEM F-11 medium supplemented with 10% FCS, 100 U/ml penicillin (Gibco-BRL), 0.1 mg/ml streptomycin (Gibco-BRL) and 2 mM glutamine.

Construction of Recombinant Virus

The recombinant adenovirus AdCA17lacZ encoding the E. coli lacZ gene under control of the human CMV promoter was obtained by homologous recombination using the pJM17 system in 293 cells (Addison et al., 1997, J. Gen. Virol., 78, 1653-1661). Recombinant vectors were plaque purified, grown to high titre in 293 cells and purified by cesium chloride banding as previously described (Hitt et al., 1995, Methods in Mol. Genetics., 7, 15-30).

Sensitizing of Cells

The THX cells ($4 \times 10^5$ cells) were seeded out in 6 cm dishes and allowed to grow overnight. At approximately 60% confluence the growth medium was exchanged with 2 ml growth medium supplemented with 20 µg/ml $AlPcS_{2a}$, and the dishes were placed back into the incubator for 16-18 hours. The sensitizer-containing medium was then sucked off, and the cells were incubated in ordinary growth medium at least 4 hours before light treatment and virus infection.

Infection of Cells

Trypsin-EDTA was used to detach cells from three dishes and the mean cell number in the dishes was calculated by Bürcher chamber counting. Adenovirus dilutions were prepared in PBS with 0.68 mm $CaCl_2$ and 0.5 mM $MgCl_2$ according to the number of cells to infect. Usually the cells were infected at an m.o.i. (multiplicity of infection) of 1 and 10.

Before virus was added the cells were exposed to red light (Philips TL 20W/09, filtered through a Cinemoid 35 filter with a light intensity reaching the cells of 1.35 mW/$cm^2$) for 3 minutes. Subsequently the medium was sucked off and 200 µl virus suspension (or PBS with 0.68 mM $CaCl_2$ and 0.5 mm $MgCl_2$ in the cases of controls not treated with virus) was added to each dish. After incubation for 30 minutes at 37° C., 5 ml ordinary growth medium was added and the cells were allowed to grow for 48 hours.

β-Galactosidase Assay

The cells were detached by Trypsin-EDTA and resuspended in 5 ml growth media. After centrifugation for 5 minutes at 1000 rpm, the medium was sucked off, the cell pellets resuspended in 50 µl growth medium and the tubes placed in a 37° C. water bath for 5 minutes. Subsequently, 50 µl of 2 mM FDG-solution preheated to 37° C. was added and the tubes placed back into the water bath for 1 minute. Finally, 900 µl growth medium was added and the tubes were incubated on ice for 30-60 minutes before the samples were analysed by flow cytometry as described above.

THX cells were treated with $AlPcS_{2a}$ (denoted as PS on FIG. 4) and adenovirus (denoted as "virus" on FIG. 4) and exposed to 3 or 4 minutes of light as described in Material and Methods and measured for β-galactosidase (β-gal) activity by flow cytometry. The total β-gal activity was quantified by integrating the β-gal positive cells and their β-gal activity. Both the number of β-gal positive cells and the mean β-gal activity was increased by the PCI treatment.

The results show that minimal infection of THX cells occurs when the cells are incubated with virus alone or virus and photosensitising agent but that photochemical treatment, i.e. the addition of light to the photosensitising agent significantly potentiates the transduction of cells (as shown by the increase in β-gal activity).

EXAMPLE 5

Photochemical Stimulation of Adenovirus-Mediated Gene Transduction $5 \times 10^4$ THX cells per well were seeded out into 6-well plates. The next day 20 μg/ml $AlPcS_{2a}$ was added, and the cells were incubated for 18 h at 37° C. All the procedures after $AlPcS_{2a}$ addition were carried on in subdued light. For the "light before" strategy, the cells were washed from $AlPcS_{2a}$ and incubated in $AlPcS_{2a}$-free medium for 4 h. Then the cells were exposed to light for 3 min before the treatment with the adenoviral vector AdHCMV-lacZ (also referred to in Example 4 as AdCA17lacZ) at a multiplicity of infection (MOI) of 1 for 30 min. This vector contains a β-galactosidase reporter gene whose expression can be analysed by flow cytometry (see below).

For the "light after" strategy $AlPcS_{2a}$-treated and washed cells were first treated with adenovirus at the same concentration and for the same time as indicated above, washed, and after addition of fresh culture medium exposed to light. Non-illuminated cells were treated in a similar way except for illumination.

The treated cells were washed once with culture medium and after addition of fresh medium incubated at 37° C. before further analysis. β-galactosidase expression was analysed by flow cytometry two days after light exposure. Detailed methods for construction of the virus (which is referred to either as AdHCMV-lacZ or AdCA17lacZ), treatment of the cells, illumination and analysis of β-galactosidase expression are described under Example 4.

The results (FIG. 5) show that the photochemical treatment using the "light before" procedure (shown by the bars on the right hand side of FIG. 5) increases the percentage of β-galactosidase-expressing cells about 6-fold; from 2.5% to 15% under these experimental conditions. It can also be seen that the effect with the "light before" procedure was almost equal to what was obtained with the "light after" method (shown by the bars on the left hand side of FIG. 5).

EXAMPLE 6

Increase in β-Galactosidase Production as a Result of PCI-Mediated Transduction with an Adenovirus Encoding β-Galactosidase The cells were grown, incubated with $AlPcS_{2a}$, infected with the virus AdHCMV-LacZ and illuminated as described under "Experimental protocols" in Example 3. To measure the production of β-galactosidase protein a chemiluminescent β-Gal reporter gene assay kit (Roche, Cat. No. 1 758 241) was used according to the manufacturer's protocol. Briefly, the cells were washed three times with precooled PBS and 1 ml of cell lysis reagent was added to each well. After incubation for 30 min at room temperature the cell extract was transferred to an eppendorf tube, centrifuged at 4° C. for 2 min at maximum speed, and 50 μl of the cell extract (supernatant) was transferred to a microtiter plate well. 100 μl substrate reagent was added, the microtiter plate was covered by foil and incubated at room temperature for 15 min to 1 h with gentle rocking. After incubation the microtiter plate was placed in a luminometer (Victor2 Wallac 1420 Multilabel Counter) and 50 μl initiation solution was injected automatically. After a delay of 1 s, the light production in 5 s was integrated. The amount of β-galactosidase was calculated from a standard curve from samples containing known amounts of β-galactosidase.

Results

FIG. 6 shows the increase in production of β-galactosidase protein that can be obtained after PCI-induced adenovirus transduction of WiDr human colon carcinoma cells.

Thus, from FIG. 6 it can be seen that at the maximal light dose an approximately 25 times increase in the production of β-galactosidase protein can be observed in the transduced cells, corresponding well with what was obtained by flow cytometry analysis (e.g. Examples 2 and 3).

EXAMPLE 7

Effect of PCI on Transduction of WiDr Cells at Different Multiplicities of Infection WiDr cells were cultivated in RPMI 1640 medium supplemented with 10% FCS (fetal calf serum), Penicillin/Streptomycin and L-glutamine. In subdued light, the medium was removed and medium containing 1 μg/ml $TPPS_{2a}$ was added. The cells (protected from light) were incubated at 37° C. for 18 h. The cells were washed three times with medium and incubated for another 3 h. The medium in the 6-well plates was removed, 200 μl of the AdHCMV-lacZ adenovirus solution was added to each well and the cells were incubated for 30 min at 37° C. (protected from light). The virus solution was removed, and the cells were washed once with medium. 2 ml medium was added and the cells were incubated for 30 min at 37° C. (protected from light). Some of the cells were exposed to 90 s of blue light with a light intensity reaching the cells of 11 mW/cm². The cells were incubated for 2 days (still protected from light) prior to analysis for β-galactosidase activity by flow cytometry as described under "Experimental protocols" in Example 3.

Results

FIG. 7 shows that with the employment of PCI it is possible to achieve 100% transduced cells even in cases where this is not possible with conventional infection using manageable virus doses. Thus, FIG. 7 shows that with WiDr cells and a virus dose of 100 MOI with PCI 100% transduction is achieved, while less that 30% transduction is obtained with conventional infection. Likewise at MOI 50, >90% transduction was achieved after PCI, while without PCI <20% transduction can be obtained.

EXAMPLE 8

Effect of PCI on Adenovirus Transduction of A549 Cells

The A549 cells were cultivated in RPMI 1640 medium supplemented with 10% FCS (fetal calf serum), Penicillin/Streptomycin and L-glutamine. In subdued light, the medium was removed and medium containing 20 μg/ml $AlPcS_{2a}$ was added. The cells (protected from light) were incubated at 37°

C. for 18 h. The cells were washed three times with medium and incubated for another 3 h. The medium was removed, 200 μl of the AdHCMV-lacZ adenovirus solution (giving an MOI of 5) was added to each well and the cells were incubated for 30 min at 37° C. (protected from light). The virus solution was removed, and the cells were washed once with medium. 2 ml medium was added and the cells were incubated for 30 min at 37° C. (protected from light). Some of the cells were exposed to red light as described under "Experimental protocols". The cells were incubated for 2 days (still protected from light) prior to analysis for β-galactosidase activity by flow cytometry as described under "Experimental protocols" in Example 3.

Results

FIG. 8 shows that PCI can enhance adenovirus-mediated gene transduction of A549 human lung cancer cells substantially. Thus, as compared to "normal infection" (the A+S– sample with 0 min light) PCI with a 6 min illumination time increased the number of transduced cells by about 11 times, from about 3% to about 33% positive cells.

EXAMPLE 9

PCI Effect on Transduction of HeLa and FinexIII Cell Lines

HeLa cells were obtained from American Type Culture Collection, and the human melanoma FinexIII cells were established at the Norwegian Radium Hospital. The cells were grown, incubated with the photosensitizer $TPPS_{2a}$ (1 μg/ml), infected with AdHCMV-lacZ adenovirus (MOI 5), illuminated and analysed as described in Example 7.

Results

FIG. 9 shows that PCI increases transduction also in the HeLa and FinexIII cell lines.

EXAMPLE 10

Effect of PCI on Transduction with Adenovirus Associated with a Poly-L-Lysine Carrier WiDr cells were grown and incubated with the photosensitizer $TPPS_{2a}$ (1 μg/ml), as described in Example 7. Poly-L-Lysine (PLL, MW 20700) was from Sigma. The concentration of virus particles in the virus preparation was determined by measuring $A_{260}$ according to Mittereder et al. (J. Virol. 1996 11:7498-7509).

The following Adenovirus/PLL-complexes were made:

5PLL/Ad: 5 molecules PLL per virus particle.

500PLL/Ad: 500 molecules PLL per virus particle.

250PLL/Ad: 250 molecules PLL per virus particle.

50PLL/Ad: 50 molecules PLL per virus particle.

A PLL dilution was added to a viral particle dilution. Samples were mixed carefully by inversion or gentle pipette tip aspiration, and incubated for 30 min in room temperature.

The medium in the 6-well plates was removed and 200 μl of the adenovirus solution or PLL/Ad solution was added to each well at an MOI of 5. The cells were incubated for 30 min at 37° C. (protected from light). Plates not infected with Adenovirus were added 200 μl PBS only. The 200 μl solution was removed, and cells were washed once with medium. 2 ml medium was added and the cells were incubated for 30 min at 37° C. (protected from light), before being exposed to blue light as described in example 7. The cells were incubated for 2 days (still protected from light) prior to analysis for β-galactosidase activity by flow cytometry as described under "Experimental protocols" in Example 3.

Results

FIG. 10 shows that PCI works also in a case where the adenovirus has been associated with the carrier poly-L-Lysine (PLL). As can be seen from FIG. 10 infection without PCI (i.e. the 0 min light doses) gave very low transduction (<5%) both with and without PLL as a carrier. It is apparent that illumination of the cells induces a light dose dependent increase in transduction both with and without the PLL, due to the PCI-effects. While the highest transduction efficiency obtained without PLL (○ on FIG. 10) was 37%, 87% positive cells could be achieved with the combination of PCI and PLL (●), representing a >20-fold increase in the percentage of transduced cells as compared to what was achieved under the same conditions without PCI, and a 100-fold increase as compared to normal infection (0 min light without PLL). Thus, PCI can substantially increase the efficiency of transduction with PLL coated adenovirus, and by using this combination a much higher transduction efficiency can be achieved than for the combination of PCI with uncoated adenovirus.

EXAMPLE 11

Effect of PCI on Adenovirus Transduction of a Human Skin Fibroblast Cell Line Employing Poly-L-Lysine as a Carrier for the Virus The HF-16 human skin fibroblast cells were grown and treated with the photosensitizer $TPPS_{2a}$ as described in Example 7. A complex of PLL and virus (250 molecules of PLL per virus particle) was made as described in Example 10, and the cells were infected at an MOI of 5, illuminated and analysed as described in Example 10.

Results

FIG. 11 shows the effect of using PCI in combination with a PLL carrier on transduction of a human skin fibroblast cell line (HF-16). Fibroblast cells are known to very resistant to adenovirus transduction and as can be seen from FIG. 11 the "normal" transduction (□, 0 s light without PLL) of these cells is very low and is enhanced to only a small degree by PCI. When PLL is employed as a carrier the transduction efficiency without light treatment increases slightly, but it can be seen that PCI in this case substantially enhances transduction, with a light-induced increase from 7.5% to 44.5% transduced cells being observed under optimal conditions. Thus, combining the use of a carrier with the PCI technology can give efficient transduction of cells that are otherwise very resistant to transduction.

EXAMPLE 12

Effect of PCI on Adenovirus Transduction using the Polycationic Dendrimer SuperFect® as a Virus Carrier WiDr cells were grown and incubated with the photosensitizer $TPPS_{2a}$ (1 μg/ml), as described in Example 7. SuperFect® was purchased from QIAGEN (3 mg/ml). The adenovirus used was AdHCMV-lacZ.

Adenovirus/SuperFect® complexes at different concentrations of SuperFect® were made by adding different amounts of SuperFect® to the adenovirus solution and incubating for 30 min at room temperature.

The medium in the 6-well plates was removed and 200 μl of adenovirus/SuperFect® complexes was added at an Adenovirus dose of MOI 5. The cells were incubated for 30 min at 37° C. (protected from light). The 200 μl solution was removed, and cells were washed once with medium. 2 ml medium was added and the cells were incubated for 30 min at 37° C. (protected from light), before being exposed to blue light as described in Example 7. The cells were incubated for 2 days (still protected from light) prior to analysis for β-galactosidase activity by flow cytometry as described under "Experimental protocols".

Results

In Example 12 we demonstrate that PCT is effective also with virus carriers other than PLL. Thus, as shown in FIG. 12 when the dendrimeric polycation SuperFect® is used as a carrier, PCI can substantially increase adenovirus-mediated gene transduction when the carrier is used in concentrations below 501 μg/ml. Maximally, with SuperFect®, PCI was able to increase the percentage of transduced cells to nearly 50 times the value obtained with "normal" infection (i.e. without PCI and without SuperFect®), while PCI without SuperFect® gave a maximal increase of 12 times and SuperFect® alone an increase of 10 times.

EXAMPLE 13

Different Time Schedules for Illumination and Administration of Adenovirus

HCT 116 cells were grown and treated with the photosensitizer $TPPS_{2a}$ as described in Example 7. The cells were infected with the Ad-HCMV-LacZ adenovirus (MOI 5) for 30 min at different time points before or after illumination (which was always 4 h after the removal of the photosensitizer). The cells were incubated further for 2 days (still protected from light) prior to analysis for β-galactosidase activity by flow cytometry as described under "Experimental protocols".

Results

FIG. 13 shows the effect of the timing of the light treatment relative to the delivery of the virus on the PCI effect on adenovirus mediated gene transduction. It can be seen (FIG. 13) that the PCI illumination is effective for a long time interval both when the virus is delivered before and when it is delivered after illumination. Thus, there is a time window of at least 17 h (from virus given 4 h before illumination to virus given 13 h after illumination) wherein the virus can be administered and illumination can be performed and where the positive PCI effect on transduction will still be maintained. This is very important from a clinical point of view because it allows the clinician great flexibility in designing the treatment and coordinating it to other treatments the patient might receive, e.g. to surgical procedures.

EXAMPLE 14

PCI Enhancement of the Gene Therapeutic Effect of an Adenovirus Vector Encoding Herpes Simplex Virus Thymidine Kinase HCT 116 adenocarcinoma cells were infected with an adenovirus gene therapy vector encoding the HSV-tk gene (AdV-TK) and subjected to PCI-treatment. Conditions for infection were as described under "Experimental protocols" (MOI=5). 2 days after infection, different concentrations of ganciclovir (GCV) was added, and the cells were incubated further for 3 days before analysis of cell survival by the MTT method. This method is based on reduction of a water-soluble tetrazolium salt (MTT) to a purple, insoluble formazan product by mitochondrial dehydrogenases present in living, metabolically active cells. One ml medium containing 0.25 μg MTT is added to the cells, followed by 4 h incubation (37° C., 5% v/v $CO_2$). The resulting formazan crystals are dissolved by adding 200 μl isopropanol (Sigma, Mo., USA) per well. The solution is transferred to a 96 wells plate which is read by a Multiskan EX microplate reader (Labsystems, Finland) with a 570 nm bandpass filter.

Results

As can be seen from FIG. 14 a light dependent increase in the toxic effect of GCV could be observed for 3 different doses of GCV in cells receiving the $AlPS_{2a}$ photosensitizer, AdV-TK and GCV. In comparison no such effect was seen in control cells receiving only photosensitizer treatment, in cells receiving photosensitizer+GCV or in cells receiving photosensitizer+AdV-TK, but no GCV. This shows that the light-induced increase in GCV-mediated cell killing is due to the increased TK gene delivery induced by the PCI treatment, leading to an increased activation of the GCV prodrug. The HSV-tk gene/GCV combination is widely used in clinical cancer gene therapy protocols and thus this example shows that PCI can be used to increase the desired cell killing effects of a gene being used in cancer gene therapy. Hence, this example shows that the gene delivery enhancing effect of PCI is not limited to reporter genes, but that it also can be used for genes encoding proteins that can execute a therapeutic effect in cancer cells.

The invention claimed is:

1. A method for introducing a nucleic acid molecule into a cell, said method comprising
    contacting said cell with a photosensitizing agent,
    contacting said cell with a nucleic acid molecule which is associated with an adenovirus, and
    irradiating said cell with light of a wavelength effective to activate the photosensitizing agent, by exposure of said cell to a light source external to said cell,
    wherein said nucleic acid molecule is part of the genome of said adenovirus or is within said adenovirus,
    wherein when said method is conducted in vivo said adenovirus is administered directly to said cell.

2. A method as claimed in claim 1 wherein said cell is mammalian.

3. A method as claimed in claim 1 wherein said nucleic acid molecule comprises a full length gene or cDNA or other DNA encoding the same, or a functional fragment thereof.

4. A method as claimed in claim 3 wherein said nucleic acid molecule encodes a prodrug activating enzyme, a protein toxin, an apoptosis inducing protein, an immune stimulating factor, a tumour specific antigen, an immune/inflammation inhibitor, an angiogenesis inhibitor, a protein inducing vessel formation, a coagulation initiating protein, an intracellular antibody or a recombinant immunotoxin.

5. A method as claimed in claim 1 wherein said nucleic acid molecule encodes an antisense RNA molecule, a ribozyme, an aptamer, an oligonucleotide or a triplex forming oligonucleotide.

6. A method as claimed in claim 3 wherein said nucleic acid molecule is 20 to 10000 bases in length.

7. A method as claimed in claim 1 wherein said nucleic acid molecule is inserted within a viral construct which contains viral derived elements necessary to enable the construct to become packaged inside the adenovirus.

8. A method as claimed in claim 1 wherein said photosensitizing agent localises to intracellular compartments, particularly endosomes or lysosomes.

9. A method as claimed in claim 1 wherein the photosensitizing agent is separate from the adenovirus.

10. A method as claimed in claim 1 wherein the photosensitizing agent is selected from the group consisting of $TPPS_{2a}$, $AlPcS_{2a}$ and other amphiphilic photo sensitizers.

11. A method as claimed in claim 1 wherein said photosensitizing agent is 5-aminolevulinic acid or an ester of 5-aminolevulinic acid or a pharmaceutically acceptable salt thereof.

12. A method as claimed in claim 1 wherein said adenovirus is contacted with said cell for 15 minutes to 6 hours.

13. A method as claimed in claim 1 wherein said photosensitizing agent is contacted with said cell for 4 to 24 hours prior to irradiation.

14. A method as claimed in claim 1 wherein the irradiation step is 1 to 10 minutes.

15. A method as claimed in claim 1 wherein said adenovirus is added before or after irradiation.

16. A method as claimed in claim 1 wherein one or both of the photosensitizing agent and the adenovirus is attached to, associated with, or conjugated to, one or more carrier molecules, targeting molecules or vectors.

17. A method as claimed in claim 16 wherein said adenovirus is attached to, associated with, or conjugated to a carrier molecule.

18. A method as claimed in claim 16 wherein said carrier molecule comprises a polycation or cationic lipid.

19. A method as claimed in claim 18 wherein said polycation is poly-L-lysine, or poly-D-lysine.

20. A method as claimed in claim 18 wherein said cationic lipid is DOTAP.

21. A method as claimed in claim 17 wherein said carrier molecule is a liposome or lipid based construct.

22. A method as claimed in claim 1 wherein the method is performed on a plurality of cells, and at least 50% of said plurality of cells into which said molecule is introduced are not killed.

23. A method as claimed in claim 1 wherein said method is performed on cells or in vivo.

24. A method of treating a cancer in a patient by gene therapy comprising introducing a nucleic acid molecule into one or more cancer cells in vitro, in vivo or ex vivo according to the method as defined in claim 1, and where necessary administering said cancer cells to said patient;

wherein said gene therapy is achieved by targeted killing of cancer cells; and wherein said targeted killing of cancer cells is achieved by use of said nucleic acid molecule, wherein said nucleic acid molecule is selected from a nucleic acid encoding a prodrug activating enzyme, a nucleic acid encoding a protein toxin, a nucleic acid encoding an apoptosis inducing protein and a nucleic acid encoding an immune stimulatory factor, wherein when said nucleic acid molecule is introduced into said cancer cells in vivo, said nucleic acid molecule which is associated with an adenovirus is injected intratumorally.

25. A method as claimed in claim 24 wherein $10^3$ to $10^{15}$ virus particles are administered in vivo.

26. An isolated cell containing a nucleic acid molecule which has been introduced into said cell by the method of claim 1.

27. A pharmaceutical composition comprising a photosensitizing agent and a nucleic acid molecule associated with an adenovirus, wherein the nucleic acid molecule is selected from a nucleic acid encoding a prodrug activating enzyme, a nucleic acid encoding a protein toxin, a nucleic acid encoding an apoptosis inducing protein, and a nucleic acid encoding an immune stimulatory factor, wherein the prodrug activating enzyme, the protein toxin, the apoptosis inducing protein, and the immune stimulating factor are not adenoviral proteins.

28. The method of claim 1, wherein the photosensitizing agent and adenovirus are contacted with said cell sequentially.

29. The method of claim 21, wherein the liposome or lipid based construct contains at least one cationic lipid.

30. The method of claim 1, wherein the nucleic acid molecule which is associated with an adenovirus is injected intratumorally and at a dose of $10^3$-$10^{15}$ virus particles per injection.

* * * * *